US012679880B2

(12) United States Patent
Westbrook

(10) Patent No.: US 12,679,880 B2
(45) Date of Patent: *Jul. 14, 2026

(54) THERAPEUTIC USE OF P75NTR NEUROTROPHIN BINDING PROTEIN

(71) Applicant: LEVICEPT LIMITED, Sandwich (GB)

(72) Inventor: Simon Westbrook, Sandwich (GB)

(73) Assignee: LEVICEPT LIMITED, Sandwich (GB)

( * ) Notice: Subject to any disclaimer, the term of this patent is extended or adjusted under 35 U.S.C. 154(b) by 14 days.

This patent is subject to a terminal disclaimer.

(21) Appl. No.: 17/659,991

(22) Filed: Apr. 20, 2022

(65) Prior Publication Data

US 2023/0093211 A1      Mar. 23, 2023

Related U.S. Application Data

(62) Division of application No. 15/326,936, filed as application No. PCT/GB2015/052083 on Jul. 17, 2015, now Pat. No. 11,339,202.

(30) Foreign Application Priority Data

Jul. 17, 2014      (GB) ...................................... 1412748

(51) Int. Cl.
| | |
|---|---|
| *C07K 14/705* | (2006.01) |
| *A61K 38/17* | (2006.01) |
| *A61K 45/06* | (2006.01) |
| *A61K 47/60* | (2017.01) |
| *A61K 47/64* | (2017.01) |

(52) U.S. Cl.
CPC .... *C07K 14/70571* (2013.01); *A61K 38/1793* (2013.01); *A61K 45/06* (2013.01); *A61K 47/60* (2017.08); *A61K 47/643* (2017.08); *A61K 47/644* (2017.08); *C07K 2319/30* (2013.01)

(58) Field of Classification Search
CPC .... A61K 38/1793; A61K 45/06; A61K 47/60; A61K 47/643; A61K 47/644; C07K 14/70571; C07K 2319/30; A61P 19/02; A61P 19/08; A61P 43/00
USPC ...................................................... 424/134.1
See application file for complete search history.

(56) References Cited

U.S. PATENT DOCUMENTS

| | | | |
|---|---|---|---|
| 8,669,350 B2 | 3/2014 | Chou | |
| 9,764,000 B2 | 9/2017 | Westbrook | |
| 9,873,728 B2 * | 1/2018 | Westbrook | ....... C07K 14/70578 |

(Continued)

FOREIGN PATENT DOCUMENTS

| | | |
|---|---|---|
| CN | 102233128 | 11/2011 |
| CN | 102586313 | 7/2012 |

(Continued)

OTHER PUBLICATIONS

Stratagene Catalog, 1988, p. 39.*

(Continued)

*Primary Examiner* — Robert B Mondesi
(74) *Attorney, Agent, or Firm* — Global Patent Group Inc.; Cynthia Hathaway

(57)      ABSTRACT

Disclosed herein are therapeutic uses of p75NTR neurotrophin binding proteins and related molecules, such as fusion proteins comprising p75NTR neurotrophin binding proteins and immunoglobulin Fc or portions thereof, in the treatment of osteoarthritis.

6 Claims, 26 Drawing Sheets

Specification includes a Sequence Listing.

(56) References Cited

U.S. PATENT DOCUMENTS

| | | | | |
|---|---|---|---|---|
| 10,683,339 | B2 | 6/2020 | Westbrook | |
| 10,751,389 | B2 * | 8/2020 | Westbrook | A61P 25/16 |
| 10,988,526 | B2 | 4/2021 | Westbrook | |
| 11,339,202 | B2 | 5/2022 | Westbrook | |
| 12,201,672 | B2 | 1/2025 | Westbrook | |
| 2007/0243132 | A1 | 10/2007 | Russell-Jones | |
| 2008/0182978 | A1 * | 7/2008 | Rosenthal | A61P 19/00 |
| | | | | 530/388.25 |
| 2009/0232808 | A1 * | 9/2009 | Priest | A61P 37/06 |
| | | | | 424/134.1 |
| 2010/0061981 | A1 * | 3/2010 | O'Leary | C07K 14/52 |
| | | | | 424/130.1 |
| 2011/0014208 | A1 | 1/2011 | Lynn | |
| 2013/0164286 | A1 | 6/2013 | Chou | |
| 2013/0336964 | A1 | 12/2013 | Rovati | |
| 2014/0017235 | A1 | 1/2014 | Rosenthal | |
| 2017/0204156 | A1 | 7/2017 | Westbrook | |
| 2021/0060123 | A1 | 3/2021 | Westbrook | |
| 2021/0238256 | A1 | 8/2021 | Westbrook | |
| 2025/0177485 | A1 | 6/2025 | Westbrook | |

FOREIGN PATENT DOCUMENTS

| | | |
|---|---|---|
| WO | 1992007076 | 4/1992 |
| WO | 2005037867 | 7/2005 |
| WO | 2006079176 | 8/2006 |
| WO | 2007026567 | 3/2007 |
| WO | 2012101664 | 8/2012 |
| WO | 2013136078 | 9/2013 |
| WO | 2015040398 | 3/2015 |
| WO | 2016009222 | 1/2016 |
| WO | 2016146841 | 9/2016 |

OTHER PUBLICATIONS

Bannwarth, B. et al. "Targeting nerve growth factor (NGF) for pain management: what does the future hold for NGF antagonists?". Drugs (2014) (Year: 2014).*

Clouet, J. et al. "From osteoarthritis treatments to future regenerative therapies for cartilage." Â Drug discovery today (2009) (Year: 2009).*

'T Hart, B. et al., "The Use of Animal Models to Investigate the Pathogenesis of Neuroinflammatory Disorders of the Central Nervous System", Curr Opin Neurol., 16(3):375-83, (2003).

Alaoui-Ismaili, M. et al., "Design of Second Generation Therapeutic Recombinant Bone Morphogenetic Proteins", Cytokine Growth Factor Rev., 20(5-6):501-7, (2009).

Amet, N. et al., "Insertion of the Designed Helical Linker Led to Increased Expression of tf-Based Fusion Proteins", Pharm Res., 26(3):523-8, (2009).

Armour, K. et al., "Recombinant human IgG molecules lacking Fcgamma receptor I binding and monocyte triggering activities", Eur J Immunol., 29(8):2613-24, (1999).

Bai, Y. et al., "Recombinant Granulocyte Colony-Stimulating Factor-Transferrin Fusion Protein as an Oral Myelopoietic Agent", Proc Natl Acad Sci., 102(20):7292-6, (2005).

Baker, M. et al., "Identification and Removal of Immunogenicity in Therapeutic Proteins", Curr Opin Drug Discov Devel., 10(2):219-27, (2002).

Barthel, C. et al., "Nerve Growth Factor and Receptor Expression in Rheumatoid Arthritis and Spondyloarthritis", Arthritis Res Ther., 11(3):R82, (2009).

Berdoz, J. et al., "Constitutive and Induced Expression of the Individual HLA-DR Beta and Alpha Chain Loci in Different Cell Types", J Immunol., 139(4):1336-41, (1987).

Bothwell, M. et al., "Dissociation Equilibrium Constant of Beta Nerve Growth Factor", J Biol Chem., 252(23):8532-6, (1977).

Bowie, J. et al., "Deciphering the Message in Protein Sequences: Tolerance to Amino Acid Substitutions", Science, 247(4948):1306-10, (1990).

Burgess, W. et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J Cell Bio., 111:2129-38, (1990).

Cell Signaling Technology, p75NTR Antibody #2693 (2010).

Chu, C. et al., "Mitochondrial Dependence of Nerve Growth Factor-Induced Mechanical Hyperalgesia", Pain, 152(8):1832-7, (2011).

Cirillo, G. et al., "Intrathecal NGF Administration Reduces Reactive Astrocytosis and Changes Neurotrophin Receptors Expression Pattern in a Rat Model of Neuropathic Pain", Cell Mol Neurobiol., 30(1):51-62, (2010).

Cowan, W., "Viktor Hamburger and Rita Levi-Montalcini: the Path to the Discovery of Nerve Growth Factor", Annu Rev Neurosci., 24:551-600, (2001).

Dray, A. et al., "Arthritis and Pain. Future Targets to Control Osteoarthritis Pain", Arthritis Research & Ther., 9(3):pp. 1-14, (2007).

EPO Preliminary Response and Claims Amendment, PCT/GB2014/052833, Jul. 20, 2015.

Fukui, Y. et al., "Low Affinity NGF Receptor (p75 Neurotrophin Receptor) Inhibitory Antibody Reduces Pain Behavior and CGRP Expression in DRG in the Mouse Sciatic Nerve Crush Model", J Orthop Res., 28(3):279-83, (2010).

Gansbacher, B. et al., "Regulation of HLA-DR, DP, and DQ Expression in Activated T Cells", Cell Immunol., 117(1):22-34, (1988).

Ghilardi, J. et al., "Sustained Blockade of Neurotrophin Receptors TrkA, TrkB and TrkC Reduces Non-Malignant Skeletal Pain but Not the Maintenance of Sensory and Sympathetic Nerve Fibers", Bone., 48(2):389-98, (2011).

Guo, H. et al., "Protein Tolerance to Random Amino Acid Change", Proc Natl Acad Sci USA, 101(25):9205-10, (2004).

Guo, J. et al., "proNGF inhibits proliferation and oligodendrogenesis of postnatal hippocampal neural stem/ progenitor cells through p 75NTR in vitro", Stem Cell Research, 11(2):874-87, (2013).

Harding, F. et al., "The Immunogenicity of Humanized and Fully Human Antibodies: Residual Immunogenicity Resides in the CDR Regions", MAbs, 2(3):256-65, (2010).

Hayashi, K. et al., "Involvement of NGF in the Rat Model of Persistent Muscle Pain Associated with Taut Band", J Pain, 12(10):1059-68, (2011).

He, X. et al., "Structure of Nerve Growth Factor Complexed with the Shared Neurotrophin Receptor p75", Science, 304(5672):870-5, (2004).

Huang, C., "Receptor-Fc Fusion Therapeutics, Traps, and Mimetibody Technology", Curr Opin Biotechnol., 20(6):692-9, (2009).

Huang, E. et al., "Trk Receptors: Roles in Neuronal Signal Transduction", Annu Rev Biochem., 72:609-42, (2003).

Ichim, G. et al., "Neurotrophins and Cell Death", Exp Cell Res., 318(11):1221-8, (2012).

International Application No. PCT/EP2016/056049; International Preliminary Report on Patentability, date of issuance Sep. 19, 2017; 7 pages.

International Application No. PCT/EP2016/056049; International Search Report and Written Opinion of the International Searching Authority, date of mailing May 23, 2016; 11 pages.

International Application No. PCT/GB2013/050632; International Preliminary Report on Patentability, date of issuance Sep. 16, 2014; 9 pages.

International Application No. PCT/GB2013/050632; International Search Report and Written Opinion of the International Searching Authority, date of mailing Jun. 6, 2013; 13 pages.

International Application No. PCT/GB2014/052833; International Preliminary Report on Patentability, date of issuance Sep. 18, 2015; 9 pages.

International Application No. PCT/GB2014/052833; International Search Report and Written Opinion of the International Searching Authority, date of mailing Dec. 17, 2014; 9 pages.

International Application No. PCT/GB2015/052083; International Preliminary Report on Patentability, date of issuance Jan. 17, 2017; 9 pages.

(56) References Cited

OTHER PUBLICATIONS

International Application No. PCT/GB2015/052083; International Search Report and Written Opinion of the International Searching Authority, date of mailing Jan. 10, 2015; 13 pages.

Iwakura, N. et al., "Role of Low-Affinity Nerve Growth Factor Receptor Inhibitory Antibody in Reducing Pain Behavior and Calcitonin Gene-Related Peptide Expression in a Rat Model of Wrist Joint Inflammatory Pain", J Hand Surg Am., 35(2):267-73, (2010).

Johnson, D. et al., "Expression and Structure of the Human NGF Receptor", Cell., 47(4):545-54, (1986).

Jung, K. et al., "Regulated Intramembrane Proteolysis of the P75 Neurotrophin Receptor Modulates its Association with the TrkA Receptor", J Biol Chem., 278(43):42161-9, (2003).

Kanning, C. et al., "Proteolytic Processing of the P75 Neurotrophin Receptor and Two Homologs Generates C-terminal Fragments with Signaling Capability", J Neurosci., 23(13):5425-36, (2003).

Kenchappa, R. et al., "P75 Neurotrophin Receptor-Mediated Apoptosis in Sympathetic Neurons Involves a Biphasic Activation of JNK and Up-Regulation of Tumor Necrosis Factor-Alpha-Converting Enzyme/ADAM17", J Biol Chem., 285(26):20358-68, (2010).

Kirschmann, D. et al., "Naturally Processed Peptides from Rheumatoid Arthritis Associated and Non-Associated HLA-DR Alleles", J Immunol., 155(12):5655-62, (1995).

Lane, N. et al., "RN624 (Anti-NGF) Improves Pain and Function in Subjects with Moderate Knee Osteoarthritis: A Hhase I Study", Arthritis & Rheumatism, 52(9 Suppl.):S461, 3 pages, (2005).

Laupéze, B. et al., "Differential Expression of Major Histocompatibility Complex Class Ia, Ib, and II Molecules on Monocytes-Derived Dendritic and Macrophagic Cells", Hum Immunol., 60(7):591-7, (1999).

Marler, K. et al., "Pro-Neurotrophins Secreted From Retinal Ganglion Cell Axons and Necessary for EphrinA-p75—Mediated Axon Guidance", Neur Dev., 5(30):10 pages, (2010).

McDonald, C. et al., "Targeting the Nogo Receptor Complex in Diseases of the Central Nervous System", Curr Med Chem., 18(2):234-44, (2011).

Nagashima, H. et al., "TNF Receptor II Fusion Protein With Tandemly Repeated Fc Domains", J Biochem., 149(3):337-46, (2011).

Ngo, J. et al., "Computational Complexity, Protein Structure Prediction and Levinthal Paradox", In Mers and Le Grand (Eds.) The Protein Folding Problem and Tertiary Structure Prediction, pp. 491-495, (1994).

Orita, S. et al., "Inhibiting Nerve Growth Factor or its Receptors Downregulates Calcitonin Gene-Related Peptide Expression in Rat Lumbar Dorsal Root Ganglia Innervating Injured Intervertebral Discs", J Orthop Res., 28(12):1614-20, (2010).

Pasut, G. et al., "Protein, Peptide and Non-Peptide Drug PEGylation for Therapeutic Application", Exper Opin Ther Patents, 14(6):859-94, (2004).

Pawson, T. et al. "Assembly of Cell Regulatory Systems Through Protein Interaction Domains", Science, 300:445-52, (2003).

Pezet, S. et al., "Differential Regulation of NGF Receptors in Primary Sensory Neurons by Adjuvant-Induced Arthritis in the Rat", Pain, 90(1-2):113-25, (2001).

Pincheira, R. et al., "The Sall2 Transcription Factor is a Novel p75NTR Binding Protein that Promotes the Development and Functipn of Neurons", Ann. N Y Acad Sci., 1144:53-5, (2008).

Rabizadeh, S. et al., "Induction of Apoptosis by the Low-Affinity NGF Receptor", Science, 261(5119):345-8, (1993).

Radeke, M. et al., "Gene Transfer and Molecular Cloning of the Rat Nerve Growth Factor Receptor", Nature, 325(6105):593-7, (1987).

Raychaudhuri, S. et al., "Nerve Growth Factor: A key Local Regulator in the Pathogenesis of Inflammatory Arthritis", Arthritis Rheum., 63(11):3243-52, (2011).

Stas, P. et al., "Immunogenicity Assessment of Antibody Therapeutics", Recombinant Antibodies for Immunotherapy, Ch. 2:20-43, (2009).

Stunz. L. et al., "HLA-DRB1 and -DRB4 genes are differentially regulated at the transcriptional level", J Immunol. 143(9):3081-6, (1989).

Svensson, P. et al., "Human Nerve Growth Factor Sensitizes Masseter Muscle Nociceptors in Female Rats", Pain, 148(3):473-80, (2010).

Tria, M. et al., "Pharmacokinetics of Nerve Growth Factor (NGF) Following Different Routes of Administration to Adult Rats", Exp Neurol., 127(2):178-83, (1994).

Truzzi, F. et al., "P75 Neurotrophin Receptor Mediates Apoptosis in Transit-Amplifying Cells and its Overexpression Restores Cell Death in Psoriatic Keratinocytes", Cell Death Differ., 18(6):948-58, (2011).

U.S. Appl. No. 14/384,302; Examiner-Initiated Interview Summary, dated May 18, 2017; 1 page.

U.S. Appl. No. 14/384,302; Notice of Allowance, dated May 18, 2017; 9 pages.

U.S. Appl. No. 15/022,505; Examiner-Initiated Interview Summary, dated Sep. 15, 2017; 1 page.

U.S. Appl. No. 15/022,505; Non-Final Office Action, dated Jan. 30, 2017; 37 pages.

U.S. Appl. No. 15/022,505; Notice of Allowance, dated Sep. 15, 2017; 10 pages.

U.S. Appl. No. 15/326,936; Corrected Notice of Allowability, dated Feb. 3, 2022; 2 pages.

U.S. Appl. No. 15/326,936; Examiner-Initiated Interview Summary, dated Dec. 9, 2021; 1 page.

U.S. Appl. No. 15/326,936; Non-Final Office Action, dated Apr. 15, 2021; 22 pages.

U.S. Appl. No. 15/326,936; Non-Final Office Action, dated Dec. 5, 2018; 17 pages.

U.S. Appl. No. 15/326,936; Notice of Allowance, dated Jan. 21, 2022; 14 pages.

U.S. Appl. No. 15/559,368; Non-Final Office Action, dated Nov. 30, 2018; 26 pages.

U.S. Appl. No. 15/559,368; Notice of Allowance, dated Feb. 6, 2020; 19 pages.

U.S. Appl. No. 15/680,872; Corrected Notice of Allowability, dated Jun. 24, 2020; 5 pages.

U.S. Appl. No. 15/680,872; Final Office Action, dated Oct. 18, 2019; 7 pages.

U.S. Appl. No. 15/680,872; Non-Final Office Action, dated Mar. 19, 2019; 17 pages.

U.S. Appl. No. 15/680,872; Notice of Allowance, dated Apr. 15, 2020; 19 pages.

U.S. Appl. No. 15/844,022; Examiner-Initiated Interview Summary, dated Oct. 3, 2019; 2 pages.

U.S. Appl. No. 15/844,022; Final Office Action, dated Oct. 3, 2019; 3 pages.

U.S. Appl. No. 15/844,022; Non-Final Office Action, dated Dec. 14, 2018; 32 pages.

U.S. Appl. No. 15/844,022; Non-Final Office Action, dated Jun. 12, 2020; 35 pages.

U.S. Appl. No. 15/844,022; Notice of Allowance, dated Dec. 28, 2020; 7 pages.

Ueda, K. et al., "Local Administration of a Synthetic Cell-Penetrating Peptide Antagonizing TrkA Function Suppresses Inflammatory Pain in Rats", J Pharmacol Sci., 112(4):438-43, (2010).

Van Walle, I. et al., "Immunogenicity Screening in Protein Drug Development", Expert Opin Biol Ther., 7(3):405-18, (2007).

Verreck, F. et al., "Natural Peptides Isolated From Gly86/Val86-Containing Variants of HLA-DR1, -DR11, -DR13, and -DR52", Immunogenetics, 43(6):392-7, (1996).

Vilar, M. et al., "Activation of the p 75 neurotrophin receptor through conformational rearrangement of disulphide-linked eceptor dimers", Neuron., 62(1):72-83, (2009).

Vilar, M. et al., "Ligand-Independent Signaling by Disulfide-Crosslinked Dimers of the p75 Neurotrophin Receptor", J Cell Sci., 122(Pt 18):3351-7, (2009).

Wang, Yong-Tang et al., "Ameliorative Effects of p75NTR-ED-Fc on Axonal Regeneration and Functional Recovery in Spinal Cord-Injured Rats," Molecular Neurobiology, Humana Press, US, 52(3):1821-34, (2014).

(56)  References Cited

OTHER PUBLICATIONS

Watanabe, T. et al., "The P75 Receptor is Associated with Inflammatory Thermal Hypersensitivity", J Neurosci Res., 86(16):3566-74, (2008).

Wells, J. "Additivity of Mutational Effects in Proteins", Biochemistry., 29(37):8509-8517, (1990).

Yamaoka, J. et al., "Changes in cutaneous sensory nerve fibers induced by skin-scratching in mice", J Dermatol Sci., 46(1):41-51, (2007).

Zampieri, N. et al. "Cleavage of p75 Neurotrophin Receptor by Alpha-Secretase and Gamma-Secretase Requires Specific Receptor Domains", J Biol Chem., 280(15):14563-71, (2005).

Zhao, H. et al., "Increasing the Homogeneity, Stability and Activity of Human Serum Albumin and Interferon-Alpha2b Fusion Protein by Linker Engineering", Protein Expr Purif., 61(1):73-7, (2008).

U.S. Appl. No. 16/929,379; Non-Final Office Action, dated Apr. 12, 2023; 19 pages.

U.S. Appl. No. 16/929,379; Notice of Allowance, dated Jun. 21, 2024; 8 pages.

U.S. Appl. No. 17/211,362; Non-Final Office Action, dated Jun. 6, 2023; 38 pages.

Hamidi, M. et al., "Pharmacokinetic Consequences of Pegylation," Drug Deliv., 13(6):399-409, (2006).

U.S. Appl. No. 15/326,936; Non-Final Office Action, dated Jul. 30, 2020; 20 pages.

U.S. Appl. No. 16/929,379; Non-Final Office Action, dated Jan. 1, 2024; 14 pages.

U.S. Appl. No. 16/929,379; Notice of Allowance, dated Sep. 11, 2024; 10 pages.

U.S. Appl. No. 17/211,362; Non-Final Office Action, dated Apr. 8, 2024; 22 pages.

Database UniProtKB Accession No. P0DOX5, "Immunoglobulin gamma-1 heavy chain"; retrieved on Sep. 26, 2025, from www.uniprot.org/uniprotkb/P0DOX5/entry#sequences; 11 pages, (last updated Jul. 18, 2018).

Hochberg, M., "Serious joint-related adverse events in randomized controlled trials of anti-nerve growth factor monoclonal antibodies", Osteoarthritis Cartilage, 23(suppl 1):S18-21, (2015).

Press Release, "Pfizer Suspends Tanezumab Osteoarthritis Clinical Trial Program", Pfizer Inc. Media, 2 pages, (Jun. 22, 2010).

U.S. Appl. No. 17/211,362; Non-Final Office Action, dated Mar. 13, 2025; 14 pages.

* cited by examiner

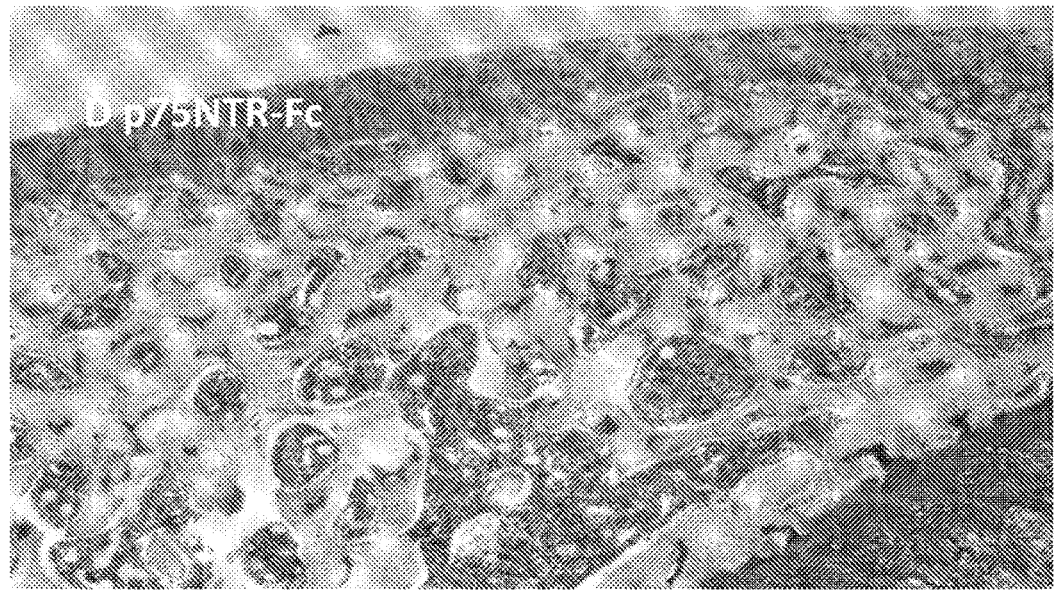
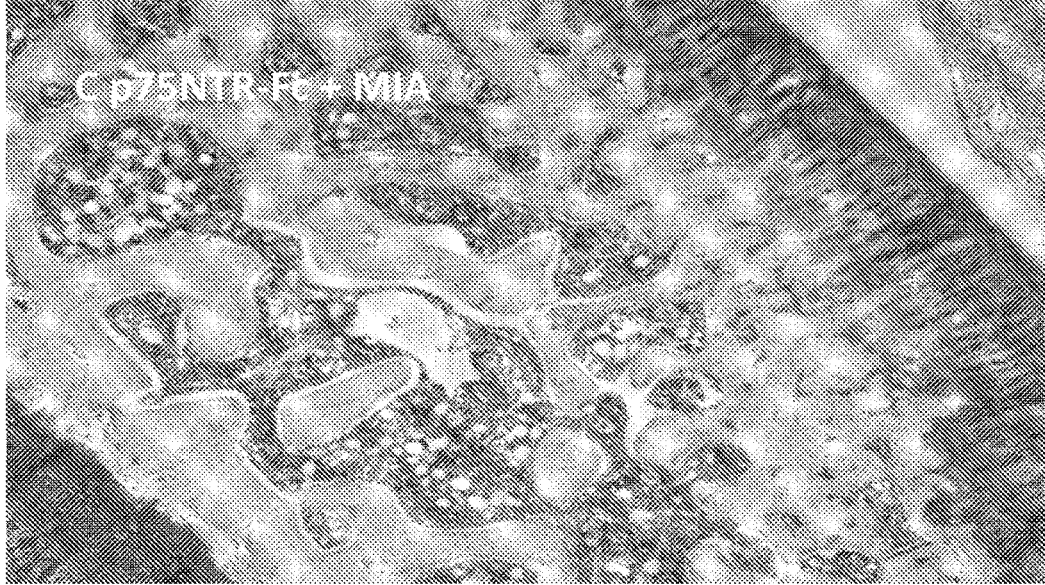
Figure 3

KEACPTGLYTHSGECCKACNLGEGVAQPCGANQTVCEPCLDSVTFSDVVSATEPCKPCTECVGLQSMS
APCVEADDAVCRCAYGYYQDETTGRCEACRVCEAGSGLVFSCQDKQNTVCEECPDGTYSDEANHVD
PCLPCTVCEDTERQLRECTRWADAECEEIPGRWITRSTPPEGSDSTAPSTQEPEAPPEQDLIASTVAGVV
TTVMGSSQPVVTRGTTDNDIEGRMD*PKSCDKTHTCPPCPAPELLGGPSVFLFPPKPKDTLMISRTPEVTC*
*VVVDVSHEDPEVKFNWYVDGVEVHNAKTKPREEQYNSTYRVVSVLTVLHQDWLNGKEYKCKVSNKALPAPIE*
*KTISKAKGQPREPQVYTLPPSRDELTKNQVSLTCLVKGFYPSDIAVEWESNGQPENNYKTTPPVLDSDGSFFL*
*YSKLTVDKSRWQQGNVFSCSVMHEALHNHYTQKSLSLSPGK*

Figure 6 – SEQ ID No. 1

MEWSWVFLFFLSVTTGVHSKEACPTGLYTHSGECCKACNLGEGVAQPCGANQTVCEPCLDSVTFSDV
VSATEPCKPCTECVGLQSMSAPCVEADDAVCRCAYGYYQDETTGRCEACRVCEAGSGLVFSCQDKQN
TVCEECPDGTYSDEANHVDPCLPCTVCEDTERQLRECTRWADAECEEIPGRWITRSTPPEGSDSTAPST
QEPEAPPEQDLIASTVAGVVTTVMGGGGEPKSSDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPG

Figure 7 – SEQ ID No. 2

KEACPTGLYTHSGECCKACNLGEGVAQPCGANQTVCEPCLDSVTFSDVVSATEPCKPCTECVGLQSMS
APCVEADDAVCRCAYGYYQDETTGRCEACRVCEAGSGLVFSCQDKQNTVCEECPDGTYSDEANHVD
PCLPCTVCEDTERQLRECTRWADAECEEIPGRWITRSTPPEGSDSTAPSTQEPEAPPEQDLIASTVAGVV
TTVMGGGG*EPKSSDKTHTCPPCPAPELLGGPSVFLFPPKPKDTLMISRTPEVTCVVVDVSHEDPEVKFNWY*
*VDGVEVHNAKTKPREEQYNSTYRVVSVLTVLHQDWLNGKEYKCKVSNKALPAPIEKTISKAKGQPREPQVYTL*
*PPSRDELTKNQVSLTCLVKGFYPSDIAVEWESNGQPENNYKTTPPVLDSDGSFFLYSKLTVDKSRWQQGNVFS*
*CSVMHEALHNHYTQKSLSLSPG*

Figure 8 – SEQ ID No. 3

AAGCTTGCCGCCACCATGGAATGGTCCTGGGTGTTCCTGTTCTTCCTGTCCGTGACCACCGGCGTG
CACTCCAAAGAGGCTTGTCCCACCGGCCTGTACACCCACTCTGGCGAGTGTTGCAAGGCCTGTAAC
CTGGGAGAAGGCGTGGCCCAGCCTTGTGGCGCTAATCAGACAGTGTGCGAGCCCTGCCTGGACTC
CGTGACCTTCTCCGATGTGGTGTCCGCCACCGAGCCTTGCAAGCCCTGCACAGAGTGTGTGGGCCT
GCAGTCCATGTCCGCCCCTTGCGTGGAAGCCGACGACGCCGTGTGTAGATGCGCCTACGGCTACTA
CCAGGACGAGACAACCGGCAGATGCGAGGCCTGCAGAGTGTGCGAAGCTGGCTCTGGCCTGGTGT
TCAGTTGTCAAGACAAGCAGAACACCGTGTGCGAGGAATGCCCCGACGGCACCTACTCTGACGAG
GCCAATCACGTGGACCCCTGCCTGCCTTGCACCGTGTGTGAAGATACCGAGCGGCAGCTGCGCGA
GTGCACCAGATGGGCTGATGCCGAGTGCGAAGAGATCCCTGGCCGGTGGATCACCAGATCCACCC
CTCCAGAGGGCTCCGACTCTACCGCTCCCTCTACCCAGGAACCTGAGGCCCCTCCTGAGCAGGACC
TGATCGCTTCTACAGTGGCCGGCGTCGTGACCACAGTGATGGGCGGAGGCGGCGAGCCTAAGTCC
TCCGACAAGACCCACACCTGTCCCCCTTGTCCTGCCCCTGAACTGCTGGGCGGACCTTCCGTGTTTC
TGTTCCCCCCAAAGCCCAAGGACACCCTGATGATCTCCCGGACCCCCGAAGTGACCTGCGTGGTGG
TGGATGTGTCCCACGAGGACCCTGAAGTGAAGTTCAATTGGTACGTGGACGGCGTGGAAGTGCAC
AACGCCAAGACCAAGCCCAGAGAGGAACAGTACAACTCCACCTACCGGGTGGTGTCTGTGCTGAC
CGTGCTGCACCAGGACTGGCTGAACGGCAAAGAGTACAAGTGCAAGGTGTCCAACAAGGCCCTGC
CAGCCCCCATCGAAAAGACCATCTCCAAGGCCAAGGGCCAGCCCCGGGAACCCCAGGTGTACACA
CTGCCCCCTAGCAGGGACGAGCTGACCAAGAACCAGGTGTCCCTGACCTGTCTCGTGAAGGGCTTC
TACCCCTCCGATATCGCCGTGGAATGGGAGTCCAACGGCCAGCCTGAGAACAACTACAAGACCAC
CCCCCCTGTGCTGGACAGCGACGGCTCATTCTTTCTGTACTCCAAGCTGACAGTGGACAAGTCCCG
GTGGCAGCAGGGCAACGTGTTCTCCTGCAGCGTGATGCACGAGGCTCTGCACAACCACTACACCC
AGAAGTCCCTGTCCCTGAGCCCCGGCTGATGAATTC

Figure 9 – SEQ ID No. 4

| | | |
|---|---|---|
| P75NTR | IASTVAGVVTTVMG | SSQPVVTRGTTDNLIPVYCSILAAVVVGLVAYIAFKR (SEQ ID 6) |
| Commercial p75-Fc | IASTVAGVVTTVMG | IPKVDKKV-EPKSCDKTHTCPPCPAPELLGGPSVFLF (SEQ ID 7) |
| p75-Fc | IASTVAGVVTTVMG | IPKVDKKV-EPKSCDKTHTCPPCPAPELLGGPSVFLF (SEQ ID 8) |
| p75-Fc C222S | IASTVAGVVTTVMG | IPKVDKKV-EPKSSDKTHTCPPCPAPELLGGPSVFLF (SEQ ID 9) |
| p75-Fc G4x1 | IASTVAGVVTTVMG | GGG------EPKSSDKTHTCPPCPAPELLGGPSVFLF (SEQ ID 10) |
| p75-Fc G4Sx1 | IASTVAGVVTTVMG | GGGS-----EPKSSDKTHTCPPCPAPELLGGPSVFLF (SEQ ID 11) |
| p75-Fc G4Sx2 | IASTVAGVVTTVMG | GGGSGGGGSEPKSSDKTHTCPPCPAPELLGGPSVFLF (SEQ ID 12) |
| Lonza IgG1za | --------------- | NTKVDKKVEPKSCDKTHTCPPCPAPELLGGPSVFLF (SEQ ID 13) |

Figure 10 – SEQ ID Nos. 6 to 13

```
1    mgagatgram dgprllllll lgvslggake acptglyths gecckacnlg egvaqpcgan
61   qtvcepclds vtfsdvvsat epckpctecv glqsmsapcv eaddavcrca ygyyqdettg
121  rceacrvcea gsglvfscqd kqntvceecp dgtysdeanh vdpclpctvc edterqlrec
181  trwadaecee ipgrwitrst ppegsdstap stqepeappe qdliastvag vvttvmgssq
241  pvvtrgttdn lipvycsila avvvglvayi afkrwnsckq nkqgansrpv nqtpppegek
301  lhsdsgisvd sqslhdqqph tqtasgqalk gdgglysslp pakreevekl lngsagdtwr
361  hlagelgyqp ehidsfthea cpvrallasw atqdsatlda llaalrriqr adlveslcse
421  statspv
```
Figure 11 – SEQ ID NO. 14 Human p75NTR full amino acid sequence

```
1    mgagatgram dgprllllll lgvslggake acptglyths gecckacnlg egvaqpcgan
61   qtvcepclds vtfsdvvsat epckpctecv glqsmsapcv eaddavcrca ygyyqdettg
121  rceacrvcea gsglvfscqd kqntvceecp dgtysdeanh vdpclpctvc edterqlrec
181  trwadaecee ipgrwitrst ppegsdstap stqepeappe qdliastvag vvttvmgssq
241  pvvtrgttdn
```
Figure 12: SEQ ID NO. 15 Human p75NTR extracellular domain including signal sequence

```
ke acptglyths gecckacnlg egvaqpcgan qtvcepclds vtfsdvvsat epckpctecv
glqsmsapcv eaddavcrca ygyyqdettg rceacrvcea gsglvfscqd kqntvceecp gtysdeanh
vdpclpctvc edterqlrec trwadaecee ipgrwitrst ppegsdstap stqepeappe
qdliastvag vvttvmgssq pvvtrgttdn
```
Figure 13: SEQ ID NO. 16 Human p75NTR extracellular domain without signal sequence

```
CAYGYYQDETTGR
```
Figure 14 SEQ ID NO. 17 Human p75NTR(NBP) neurotrophin binding domain 1

```
VCEAGSGLVFSCQD KQNTVCEECP GGTYSDEANH VDPCLPCTVCEDTER
```
Figure 15 SEQ ID NO. 18 Human p75NTR(NBP) neurotrophin binding domain 2

```
VCEAGSGLVFSCQDK
```
Figure 16 SEQ ID NO.19 Human p75NTR(NBP) neurotrophin binding domain 3

```
WADAECEEIPGR
```
Figure 17 SEQ ID NO. 20 Human p75NTR(NBP) neurotrophin binding domain 4

```
LDSVTSDVVSATEPCKP
```
Figure 18 SEQ ID NO. 21 Human p75NTR(NBP) neurotrophin binding domain 5

```
  1 mrlavgallv cavlgiclav pdktvrwcav seheatkcqs frdhmksvip sdgpsvacvk
 61 kasyldcira iaaneadavt ldaglvyday lapnnlkpvv aefygskedp qtfyyavavv
121 kkdsgfqmnq lrgkkschtg lgrsagwnip igllycdlpe prkplekava nffsgscapc
181 adgtdfpqlc qlcpgcgcst lnqyfgysga fkclkdgagd vafvkhstif enlankadrd
241 qyellcldnt rkpvdeykdc hlaqvpshtv varsmggked liwellnqaq ehfgkdkske
301 fqlfssphgk dllfkdsahg flkvpprmda kmylgyeyvt airnlregtc peaptdeckp
361 vkwcalshhe rlkccdewsvn svgkiecvsa ettedciaki mngeadamsl dggfvyiagk
421 cglvpvlaen ynksdncedt peagyfavav vkksasdltw dnlkgkksch tavgrtagwn
481 ipmgllynki nhcrfdeffs egcapgskkd sslcklcmgs glnlcepnnk egyygytgaf
541 rclvekgdva fvkhqtvpqn tggknpdpwa knlnekdyel lcldgtrkpv eeyanchlar
601 apnhavvtrk dkeacvhkil rqqqhlfgsn vtdcsgnfcl frsetkdllf rddtvclakl
661 hdrntyekyl geeyvkavgn lrkcstssll eactfrrp
```
Figure 19 SEQ ID NO. 22 Human Transferrin

```
  1 mkwvtfisll flfssaysrg vfrrdahkse vahrfkdlge enfkalvlia faqylqqcpf
 61 edhvklvnev tefaktcvad esaencdksl htlfgdklct vatlretyge madccakqep
121 ernecflqhk ddnpnlprlv rpevdvmcta fhdneetflk kylyeiarrh pyfyapellf
181 fakrykaaft eccqaadkaa cllpkldelr degkassakq rlkcaslqkf gerafkawav
241 arlsqrfpka efaevsklvt dltkvhtecc hgdllecadd radlakyice nqdsissklk
301 eccekpllek shciaevend empadlpsla adfveskdvc knyaeakdvf lgmflyeyar
361 rhpdysvvll lrlaktyett lekccaaadp hecyakvfde fkplveepqn likqncelfe
421 qlgeykfqna llvrytkkvp qvstptlvev srnlgkvgsk cckhpeakrm pcaedylsvv
481 lnqlcvlhek tpvsdrvtkc cteslvnrrp cfsalevdet yvpkefnaet ftfhadictl
541 sekerqikkq talvelvkhk pkatkeqlka vmddfaafve kcckaddket cfaeegkklv
601 aasqaalgl
```
Figure 20 SEQ ID NO. 23 Human Albumin

```
  1 ggpsvflfpp kpkdtlmisr tpevtcvvvd vshedpevkf nwyvdgvevh naktkpreeq
 61 ydstyrvvsv ltvlhqdwln gkeykckvsn kalpapiekt iskakgqpre pqvytlppsr
121 eemtknqvsl tclvkgfyps diavewesng qpennykttp pvldsdgsff lyskltvdks
181 rwqqgnvfsc svmhealhnh ytqkslslsp gk
```
Figure 21. SEQ ID NO. 24 Human Fc IgG1

```
  1 astkgpsvfp lapcsrstse staalgclvk dyfpepvtvs wnsgaltsgv htfpavlqss
 61 glyslssvvt vtssnfgtqt ytcnvdhkps ntkvdktver kccvecppcp appvagpsvf
121 lfppkpkdtl misrtpevtc vvvdvshedp evqfnwyvdg mevhnaktkp reeqfnstfr
181 vvsvltvvhq dwlngkeykc kvsnkglpap iektisktkg qprepqvytl ppsreemtkn
241 qvsltclvkg fypsdiavew esngqpenny kttppmldsd gsfflysklt vdksrwqqgn
301 vfscsvmhea lhnhytqksl slspgk
```

Figure 22. SEQ ID NO. 25 Human Fc IgG2

```
  1 cytllllttp swvlsqvtik esgpvlvkpt etltltctvs gfslsnakmg vswirqppgk
 61 alewlahifs ndeksystsl ksrltiskdt sksqvvltmt nmdpvdtaty ycariftity
121 snyvlqyyyy mdvwgkgttv tvssastkgp svfplapcsr stsgg
```

Figure 23. SEQ ID NO. 26 Human Fc IgG3

```
  1 apeflggpsv flfppkpkdt lmisrtpevt cvvvdvsqed pevqfnwyvd gvevhnaktk
 61 preeqfnsty rvvsvltvlh qdwlngkeyk ckvsnkglps siektiskak gqprepqvyt
121 lppsqeemtk nqvsltclvk gfypsdiave wesngqpenn ykttppvlds dgsfflyskl
181 tvdksrwqeg nvfscsvmhe alhnhytqks lslslgk
```

Figure 24. SEQ ID NO. 27 Human Fc IgG4

```
  1 ggpsvflfpp kpkdtlyitr epevtcvvvd vshedpevkf nwyvdgvevh naktkpreeq
 61 ynstyrvvsv ltvlhqdwln gkeykckvsn kalpapiekt iskakgqpre pqvytlppsr
121 deltknqvsl tclvkgfyps diavewesng qpennykttp pvldsdgsff lyskltvdks
181 rwqqgnvfsc svmhealhnh ytqkslsls
```

Figure 25. SEQ ID NO. 28 Human Fc Fragment Engineered For Extended Serum Half-Life

```
  1 thtcppcpap efeggpsvfl fppkpkdtlm isrtpevtcv vvdvshedpe vkfnwyvdgv
 61 evhnaktkpr eeqynstyrv vsvltvlhqd wlngkeykck vsnkalpasi ektiskakgq
121 prepqvytlp psreemtknq vsltclvkgf ypsdiavewe sngqpennyk ttppvldsdg
181 sfflyskltv dksrwqqgnv fscsvmheal hnhytqksls lspgk
```

Figure 26. SEQ ID NO. 29 Human Fc Fragment Engineered For Lack Of Effector Functions

(GGGGS)$n$ ($n$ = 1 to 4)

Figure 27: SEQ ID NO. 30 p75NTR(NBP)-Fc linker

(EAAAK)$n$ ($n$ = 2 to 5)

Figure 28: SEQ ID NO. 31 p75NTR(NBP)-Fc linker

GGGGS

Figure 29: SEQ ID NO. 32 p75NTR(NBP)-Fc linker

Left Knee                    Right Knee

Control IgG-Fc treated animals - Day 56

Left Knee                    Right Knee 3 mg/kg PG-007 treated animals - Day 56

Left Knee                    Right Knee 3 mg/kg p75NTR-Fc treated animals – Day 56

1 mg/kg p75NTR-Fc treated animals – Day 56

Left Knee             Right Knee 0.3 mg/kg p75NTR-Fc treated animals – Day 56

THERAPEUTIC USE OF P75NTR NEUROTROPHIN BINDING PROTEIN

FIELD OF THE INVENTION

The present invention relates to a new therapeutic use of a p75NTR neurotrophin binding protein and related molecules in the treatment of osteoarthritis.

BACKGROUND TO THE INVENTION

Osteoarthritis is a group of conditions in which the joints are degraded, leading to pain, tenderness, stiffness and locking of joints. It is the most common form of arthritis, affecting millions of people around the world.

The condition is generally accepted to be the result of mechanical damage to cartilage in joints with inadequate self repair. In addition to leading to inflammation, pain and swelling, the loss of cartilage can lead to the formation of bone outgrowths (osteophytes) which exacerbate symptoms and can lead to narrowing and distortion of the joint. The precise mechanisms of cartilage damage and loss are not precisely understood and may be the result of a combination of factors.

Treatment of osteoarthritis is limited to management of the condition, with no curative treatment options available. There are also no reported treatments which halt progression of this degenerative disease. Management options include physiotherapy, administration of pain killers and/or administration of anti-inflammatory drugs and, in some cases, joint replacement via surgery.

The neurotrophins, neurotrophic growth factor (NGF), brain-derived neurotrophic factor (BDNF), neurotrophin 3 (NT-3), and neurotrophin 4/5 (NT-4/5) act via four receptors: the low affinity p75 neurotrophin receptor (p75NTR), and the high affinity tyrosine kinase receptors; TrkA, TrkB, and TrkC. The low affinity receptor p75NTR binds and is activated by all four neurotrophins and has been reported to function independently from the other receptors. However, the Trk receptors are more selectively activated i.e. NGF is the selective ligand for TrkA, BDNF the ligand for TrkB and NT-3, 4/5 the ligands for TrkC. In addition it has been reported, when p75NTR and Trk proteins are co-expressed, they form complexes, which alter the signalling of both receptors (Huang and Reichardt, 2003). Indeed, it has been suggested that p75NTR facilitates the selectivity of each of the neurotrophins for their respective Trk receptor.

The p75NTR is a member of the tumor necrosis factor receptor superfamily (TNFR-SF) and was the first member of this superfamily to be characterized fully. The superfamily (encoded by some 30 genes in humans) is defined by ligand-binding domains consisting of one or more (typically four) repeats of a 40 amino acid cysteine-rich domain (CRD) that was first identified in p75NTR (Johnson et al., 1986; Radeke et al., 1987). In contrast, no sequence motif is shared by the intracellular domains of all TNFR-SF family members. Consequently, signalling mechanisms of TNFR-SF proteins vary significantly.

An unusual feature of p75NTR structure is the existence of a disulfide-linked p75NTR dimer, formed via cysteinyl residues within the transmembrane domains. This disulfide linkage is required for effective neurotrophin-dependent signalling by p75NTR and plays an important role in the formation of an intracellular and extracellular domain (Vilar et al., 2009b). Neurotrophins exist physiologically as non-covalently associated dimers (Bothwell and Shooter, 1977) with a distribution half-life of approximately 5 min (Tria et al., 1994). Neurotrophin-dependent p75NTR activation involves association of a neurotrophin dimer with CRDs 2-4 of the two extracellular domains of a p75NTR dimer (He and Garcia, 2004). Recent studies support a model in which neurotrophin binding causes the two extracellular domains of p75NTR dimers to move closer together, forcing the intracellular domains to splay apart in a snail-tong-like motion centered on the disulfide bond and permitting association of the intracellular domains with the signalling adapter proteins, NRIF and TRAF6 (Vilar et al., 2009a, 2009b). Intra-transmembrane domain disulfide bonds, such as are present in p75NTR, have not been described previously in other TNFR-SF family members, or in any other membrane protein.

p75NTR undergoes sequential proteolytic cleavage by alpha-secretase and gamma-secretase activities and matrix metalloproteinases (MMPs), releasing its intracellular domain (ICD) into the cytoplasm, in a manner analogous to the cleavage-dependent signalling pathway of Notch and beta-amyloid precursor protein (Jung et al., 2003; Kanning et al., 2003). Cytoplasmic release of the p75NTR ICD by this pathway promotes signalling by associated NRIF (Kenchappa et al., 2006). The role of the extracellular domain of p75NTR, following the proteolytic cleavage by alpha-secretase and gamma-secretase activities and MMPs is not fully understood.

It has been documented that NGF and other neurotrophins (BDNF, NT-3 and NT-4/5) play a significant role in pathology for example pain due to osteoarthritis, pancreatitis, rheumatoid arthritis, psoriasis, pruritis and multiple sclerosis (Watanabe et al., 2010; Raychaudhuri et al., 2011; Barthel et al., 2009; Truzzi et al., 2011; McDonald et al., 2011; Yamaoka et al., 2007). It was been demonstrated that selective antibodies to any of the neurotrophins; either NGF or BDNF, NT-3 and NT-4/5 significantly reduce pain. Furthermore, antibodies directed to the neurotrophin receptors p75NTR Trk A, Trk B or Trk C have also been demonstrated to be efficacious in models of pain (Orita S et al., 2010; Svensson P et al., 2010; Iwakura et al., 2010; Cirillo et al., 2010; Pezet et al., 2010; Hayashi et al., 2011; Chu et al., 2011; Ueda et al., 2010; Ghilardi et al., 2010; Fukui et al., 2010). Fukui et al., (2010) in a model of pain (mechanical allodynia following sciatic nerve crush) demonstrated significant efficacy on pain related endpoints following treatment with an anti-p75NTR antibody. It was concluded from this study that the treatment with a p75NTR inhibitory antibody reduced CGRP and p75NTR expression resulting in a significant reduction in pain.

BRIEF DESCRIPTION OF THE INVENTION

The current invention demonstrates the extracellular domain of p75NTR is useful in the treatment of osteoarthritis. The extracellular domain of p75NTR has been shown to halt and even reverse the progression of the disease.

Accordingly, there is provided in a first aspect a p75NTR neurotrophin binding protein (p75NTR(NBP)) for use in the treatment of osteoarthritis.

In preferred embodiments, the treatment of osteoarthritis includes relief from the symptoms of osteoarthritis. Preferably relief from the symptoms of osteoarthritis include, but are not limited to reduction in pain, inflammation, swelling, tenderness, joint stiffness or increase in joint mobility or any combination of these.

In a particularly preferred embodiment, treatment of osteoarthritis includes slowing or arresting of disease progression and/or reduction in cartilage loss. Preferably treatment of osteoarthritis includes reversal of disease progression, regrowth of cartilage and/or curative treatment. Preferably disease progression is determined by the rate of cartilage loss or regrowth. In other preferred embodiments, disease progression may be monitored by determining the number of chondrocytes present in a joint.

In other preferred embodiments, the treatment of osteoarthritis includes prophylactic treatment.

In certain preferred embodiments the p75NTR(NBP) is a human p75NTR(NBP).

In other preferred embodiments the p75NTR(NBP) comprises a p75NTR(NBP) connected to one or more auxiliary molecules. Preferably, the one or more auxiliary molecules are selected from: (a) transferrin or a portion thereof; (b) albumin or a portion thereof; (c) an immunoglobulin Fc or a portion thereof; or (d) a polyethylene glycol polymer chain.

In still other preferred embodiments the p75NTR(NBP) is connected to the one or more auxiliary molecules via one or more linkers.

In an especially preferred embodiment the p75NTR(NBP) has the amino acid sequence according to SEQ ID NO 3.

In a particularly preferred embodiment the p75NTR (NBP) binds to any of NGF, BDNF, NT3 or NT4/5 with a binding affinity ($K_d$) of between about 5 pM to about 5 nM as measured by surface plasmon resonance at 20° C.

In a preferred embodiment the p75NTR(NBP) is for separate, sequential or simultaneous use in a combination combined with a second pharmacologically active compound. Preferably the second pharmacologically active compound of the combination is selected from an opioid analgesic, a nonsteroidal anti-inflammatory drug (NSAID), a barbiturate sedative, a benzodiazepine having a sedative action, an H1 antagonist having a sedative action, a sedative such as glutethimide, meprobamate, methaqualone or dichloralphenazone; a skeletal muscle relaxant; an NMDA receptor antagonist, an alpha-adrenergic, a tricyclic antidepressant, an anticonvulsant, a tachykinin (NK) antagonist, particularly an NK-3, NK-2 or NK-1 antagonist, a muscarinic antagonist, a COX-2 selective inhibitor, a coal-tar analgesic, in particular paracetamol; a neuroleptic a vanilloid receptor agonist or antagonist; a beta-adrenergic; a local anaesthetic; a corticosteroid; a 5-HT receptor agonist or antagonist; a 5-HT2A receptor antagonist; a cholinergic (nicotinic) analgesic; Tramadol®; a PDEV inhibitor; a cannabinoid; metabotropic glutamate subtype 1 receptor (mGluR1) antagonist; a serotonin reuptake inhibitor; a noradrenaline (norepinephrine) reuptake inhibitor; a dual serotonin-noradrenaline reuptake inhibitor; an inducible nitric oxide synthase (iNOS) inhibitor; an acetylcholinesterase inhibitor; a prostaglandin E2 subtype 4 (EP4) antagonist; a leukotriene B4 antagonist; a 5-lipoxygenase inhibitor; a sodium channel blocker; or a 5-HT3 antagonist, and the pharmaceutically acceptable salts and solvates thereof.

Preferably the p75NTR(NBP) is formulated for oral, sublingual, buccal, topical, rectal, inhalation, transdermal, subcutaneous, intravenous, intra-arterial, intramuscular, intracardiac, intraosseous, intrasynovial, intradermal, intraperitoneal, transmucosal, vaginal, intravitreal, intra-articular, peri-articular, local or epicutaneous administration.

In a further aspect of the present invention there is provided a nucleic acid encoding a p75NTR(NBP), for use in the treatment of osteoarthritis as defined above.

In another aspect of the present invention there is provided a replicable expression vector for transfecting a cell, comprising a nucleic acid encoding a p75NTR(NBP), for use in the treatment of osteoarthritis as defined above.

In yet another aspect of the present invention there is provided a host cell expressing a p75NTR(NBP), for use in the treatment of osteoarthritis as defined above.

In a still further aspect of the present invention there is provided a pharmaceutical composition, comprising the p75NTR(NBP), the nucleic acid molecule, the replicable expression vector, or the host cell described above, and a pharmaceutically acceptable carrier and/or an excipient.

Another aspect of the invention pertains to a kit comprising:

a. the p75NTR(NBP), the nucleic acid molecule, the replicable expression vector, the host cell, or the pharmaceutical composition described above; and b. instructions for the administration of an effective amount of the p75NTR(NBP), nucleic acid molecule, replicable expression vector or pharmaceutical composition to an individual for any one or more of the prevention or treatment of osteoarthritis and/or a symptom of osteoarthritis or for ameliorating, controlling, reducing incidence of, or delaying or reversing the development or progression of osteoarthritis and/or a symptom of osteoarthritis.

In another aspect of the present invention there is provided a method of treating and/or preventing osteoarthritis and/or a symptom of osteoarthritis in an individual comprising administering to said individual a therapeutically effective amount of the p75NTR(NBP), the nucleic acid molecule, the replicable expression vector, the host cell, or the pharmaceutical composition described above, optionally further comprising a pharmaceutically acceptable carrier.

DESCRIPTION OF FIGURES

The present invention will be further understood by reference to the attached figures, in which:

FIG. 6: Amino acid sequence of a p75NTR(NBP)-Fc fusion protein (SEQ ID No. 1). The alpha and gamma secretase cleavage sites are shown in bold type. The IgG1 Fc portion is shown in italics.

FIG. 7: Translation product (SEQ ID No. 2), from start to stop codons, of the nucleic acid sequence set forth in FIG. 9 (SEQ ID No. 4).

FIG. 8: Amino acid sequence of a preferred p75NTR (NBP)-Fc fusion protein (SEQ ID No. 3). The IgG1 Fc portion is shown in italics. The linker sequence between the p75NTR(NBP) and Fc portions is shown underlined.

FIG. 9: Nucleic acid sequence of full product gene from 5' cloning site to 3' cloning site (SEQ ID No. 4)

FIG. 10: p75-NTR(NBP)-Fc fusion protein variants: 1: p75_NTR—The p75-NTR sequence (SEQ ID No. 6); 2: Commercially available p75-NTR-Fc fusion protein (SEQ ID No. 7); 3: p75_Fc—The commercially available p75-NTR-Fc fusion protein with the Fc sequence modified to that of the Lonza constant region of IgGiza (SEQ ID No. 8); 4: p75_Fc_C222S—The commercially available p75-NTR-Fc fusion protein with the Fc sequence modified to that of the Lonza constant region of IgGiza and an additional cysteine to serine mutation at position 222 (SEQ ID No. 9); 5: p75_Fc_G4x1—Variant 1, a proposed p75-NTR-Fc fusion protein with a four residue glycine linker (SEQ ID No. 10); 6: p75_Fc_G4Sx1—variant 2, a proposed p75-NTR-Fc fusion protein with a single tetra-glycine serine linker (SEQ ID No. 11); 7: p75_Fc_G4Sx2—variant 3, a proposed p75-NTR-Fc fusion protein with two tetra-glycine serine linkers (SEQ ID No. 12); 8: Lonza constant region of IgGiza (SEQ ID No. 13).

Figure 1:
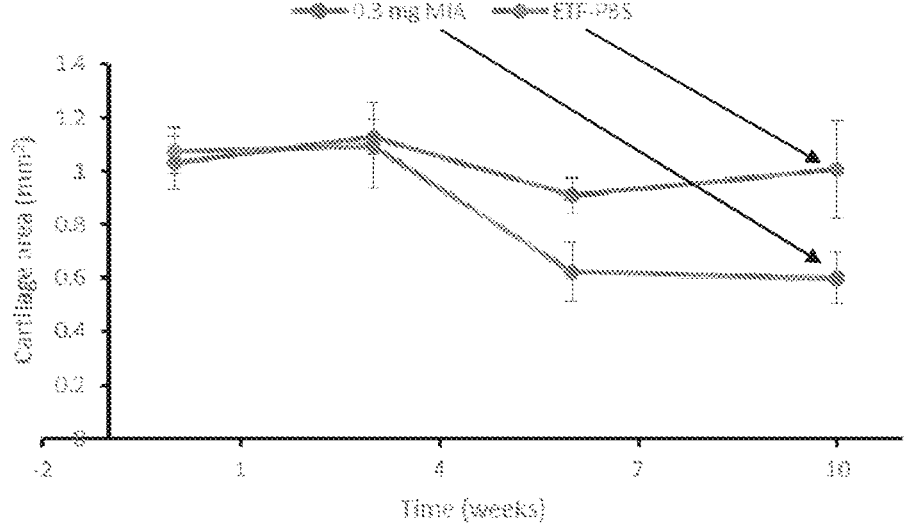
FIG. 1: Progression of loss of cartilage area following injection of MIA or ETF-PBS. Data points are mean±SEM, n=6

In this alignment a formatting scheme is used to highlight regions of similarity between the putative receptors, the Fc-fusion protein and the Fc constant region: Boxed type is used to indicate regions of identical sequence between the variant proteins and the p75-NTR; Single underlining is used to indicate regions of identical sequence between all of the Fc-fusion proteins and the Lonza IgGiza Fc; Italics are used to indicate linker regions at the junction of the p75-NTR and the Fc constant region; Double-underlining and bold type are used to indicate the position of non-identical sequence outside the linker region, at the position equivalent to 222 in the parental p75-NTR Fc-fusion protein.

FIG. 11: SEQ ID NO. 14 Human p75NTR full amino acid sequence

FIG. 12: SEQ ID NO. 15 Human p75NTR extracellular domain including signal sequence FIG. 13: SEQ ID NO. 16 Human p75NTR extracellular domain without signal sequence FIG. 14: SEQ ID NO. 17 Human p75NTR(NBP) neurotrophin binding domain 1

FIG. 15: SEQ ID NO. 18 Human p75NTR(NBP) neurotrophin binding domain 2

FIG. 16: SEQ ID NO. 19 Human p75NTR(NBP) neurotrophin binding domain 3

FIG. 17: SEQ ID NO. 20 Human p75NTR(NBP) neurotrophin binding domain 4

FIG. 18: SEQ ID NO. 21 Human p75NTR(NBP) neurotrophin binding domain 5

FIG. 19: SEQ ID NO. 22 Human Transferrin

FIG. 20: SEQ ID NO. 23 Human Albumin

FIG. 21: SEQ ID NO. 24 Human Fc IgG1

FIG. 22: SEQ ID NO. 25 Human Fc IgG2

FIG. 23: SEQ ID NO. 26 Human Fc IgG3

FIG. 24: SEQ ID NO. 27 Human Fc IgG4

Figure 30:
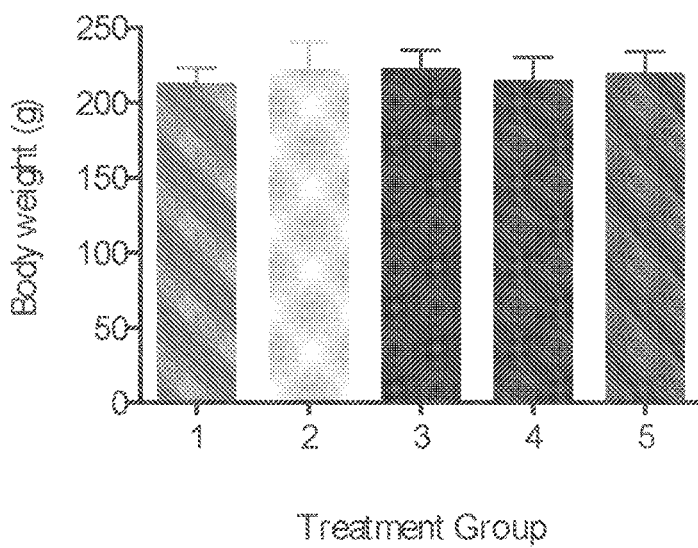

FIG. 25: SEQ ID NO. 28 Human Fc Fragment Engineered For Extended Serum Half-Life FIG. 26: SEQ ID NO. 29 Human Fc Fragment Engineered For Lack Of Effector Functions FIG. 27: SEQ ID NO. 30 p75NTR(NBP)-Fc linker FIG. 28: SEQ ID NO. 31 p75NTR(NBP)-Fc linker FIG. 29: SEQ ID NO. 32 p75NTR(NBP)-Fc linker FIG. 30: Mean body weight at day 0. Weight in grams are plotted as mean±standard deviations. Animals in Group 1 were treated with 1 mg/kg p75NTR-Fc, Group 2 with 3 mg/kg p75NTR-Fc, Group 3 with 0.3 mg/kg p75NTR-Fc, Group 4 with 3 mg/kg PG-007 and Group 5 with 3 mg/kg Control IgG Fc.

Figure 31:
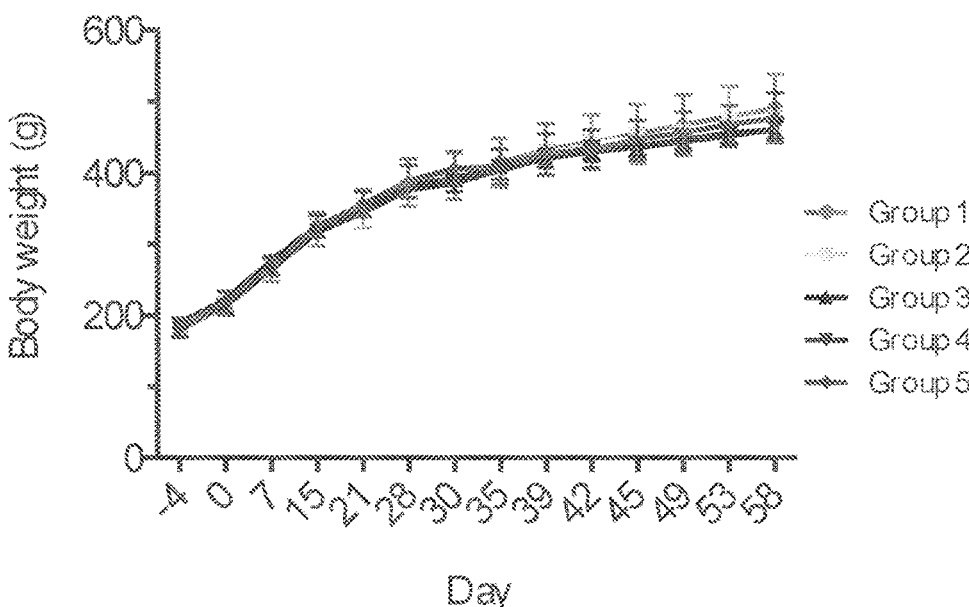

FIG. 31: Mean body weight of rats during the eight week study described in Example 3. Weight in grams are plotted as mean k standard deviations. Animals in Group 1 were treated with 1 mg/kg p75NTR-Fc, Group 2 with 3 mg/kg p75NTR-Fc, Group 3 with 0.3 mg/kg p75NTR-Fc, Group 4 with 3 mg/kg PG-007 and Group 5 with 3 mg/kg Control IgG Fc.

Figure 32:
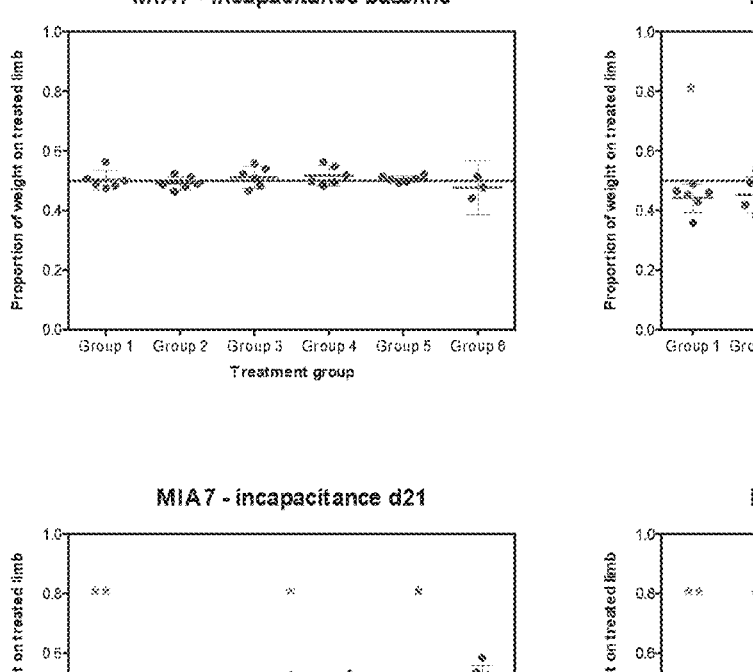

FIG. 32: Spontaneous pain measurements determined with time following treatment with test agents. Data is shown for each animal at each timepoint (from day 35 to day 56). Animals in Group 1 were treated with 1 mg/kg p75NTR-Fc, Group 2 with 3 mg/kg p75NTR-Fc, Group 3 with 0.3 mg/kg p75NTR-Fc, Group 4 with 3 mg/kg PG-007, Group 5 with 3 mg/kg Control IgG Fc, Group 6 with ETF-PBS and Group 7 were naïve. *$p<0.05$ and **$<0.01$ for one sample t-test against the theoretical mean of 0.5.

Figure 33:
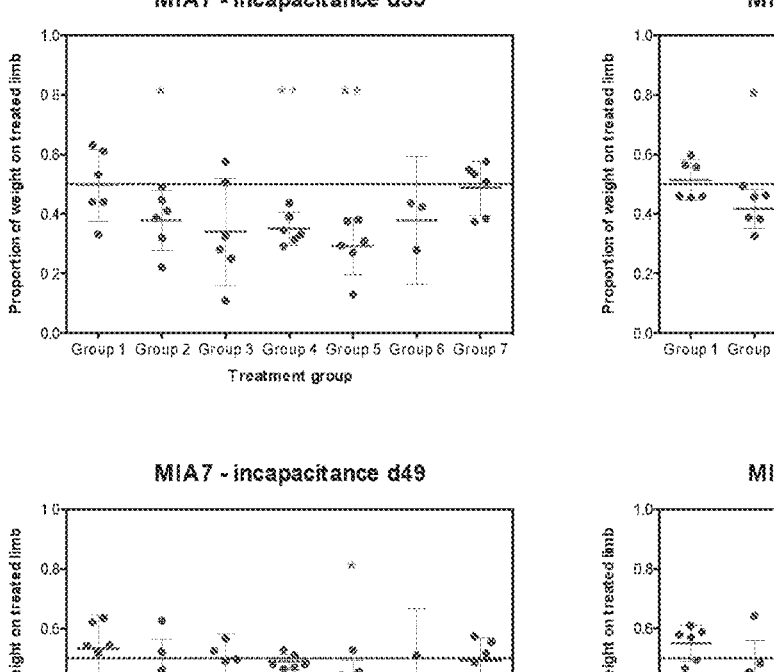

FIG. 33: Spontaneous pain measurements determined with time following treatment with test agents. Data is shown for each animal at each timepoint (from day 35 to day 56). Animals in Group 1 were treated with 1 mg/kg p75NTR-Fc, Group 2 with 3 mg/kg p75NTR-Fc, Group 3 with 0.3 mg/kg p75NTR-Fc, Group 4 with 3 mg/kg PG-007, Group 5 with 3 mg/kg Control IgG Fc, Group 6 with ETF-PBS and Group 7 were naïve. *$p<0.05$ and **$<0.01$ for one sample t-test against the theoretical mean of 0.5.

Figure 34:
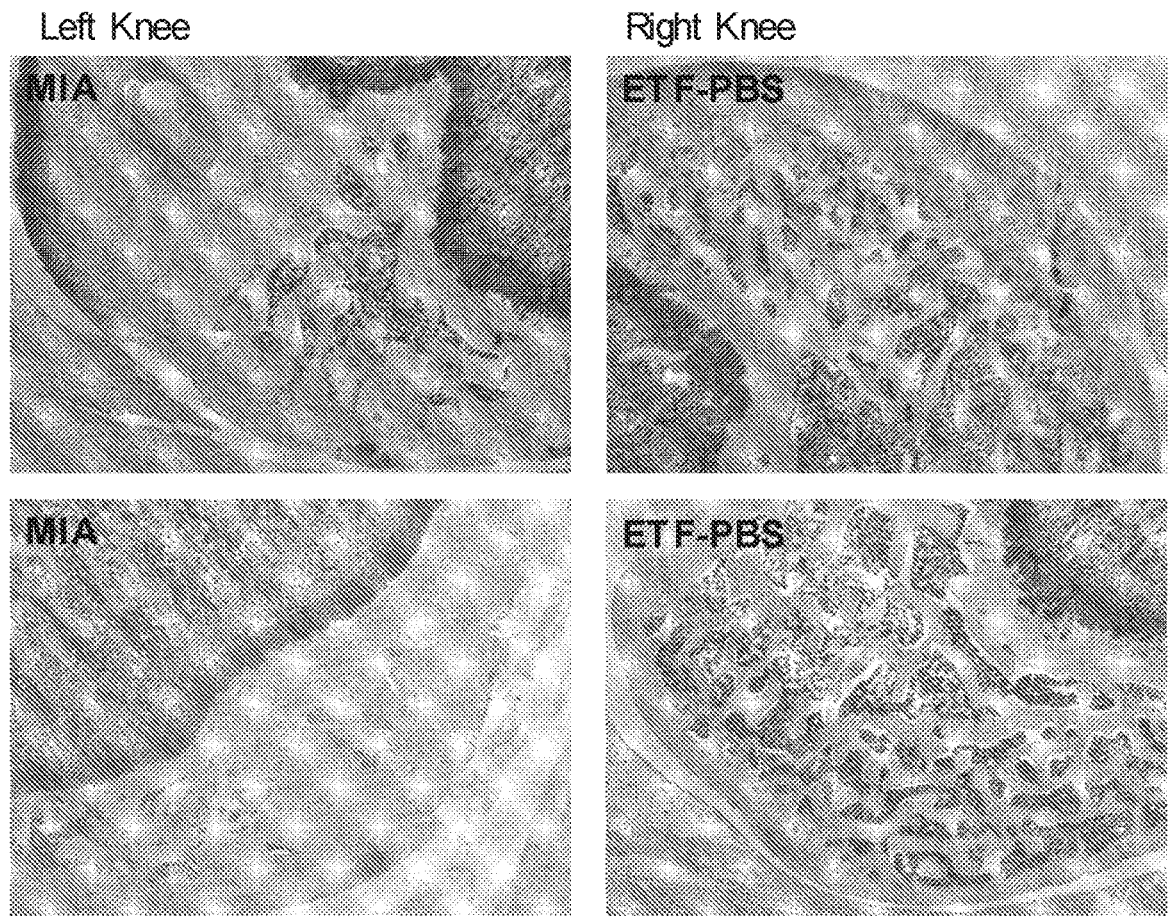

FIG. 34: Medial aspect of the rat knee stained with Safranin O Fast Green from animals treated with 3 mg/kg control IgG-Fc from day 28 to day 56 following a low MIA or ETF-PBS injection on day 0 into the knee (×4 magnification). Representative images are taken from animals treated with 3 mg/kg control IgG-Fc. Each set of left and right knee image are taken from one individual animal to show the contralateral control.

Figure 35:
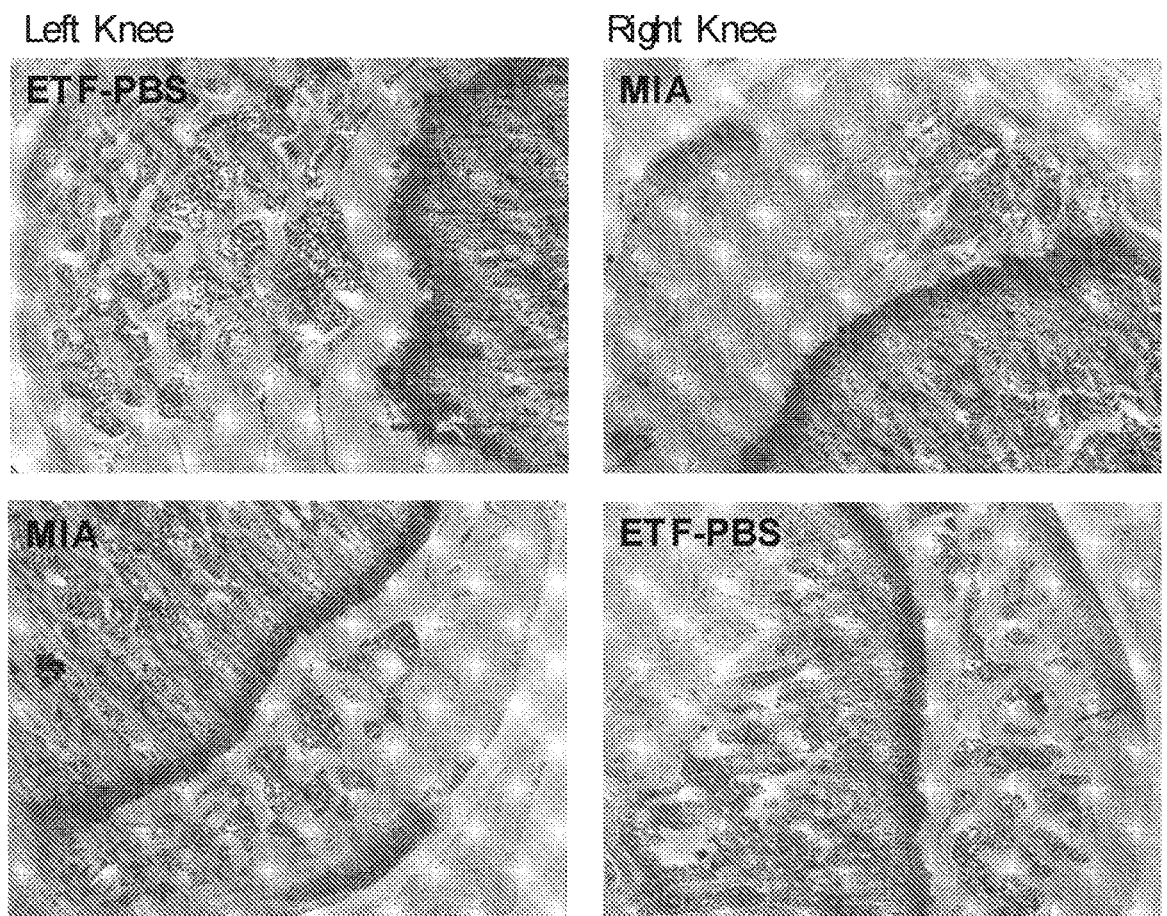

FIG. 35: Medial aspect of the rat knee stained with Safranin O Fast Green from animals treated with 3 mg/kg PG-007 from day 28 to day 56 following a low MIA or ETF-PBS injection on day 0 into the knee (×4 magnification). Representative images are taken from animals treated with 3 mg/kg PG-007. Each set of left and right knee image are taken from one individual animal to show the contralateral control.

Figure 36:
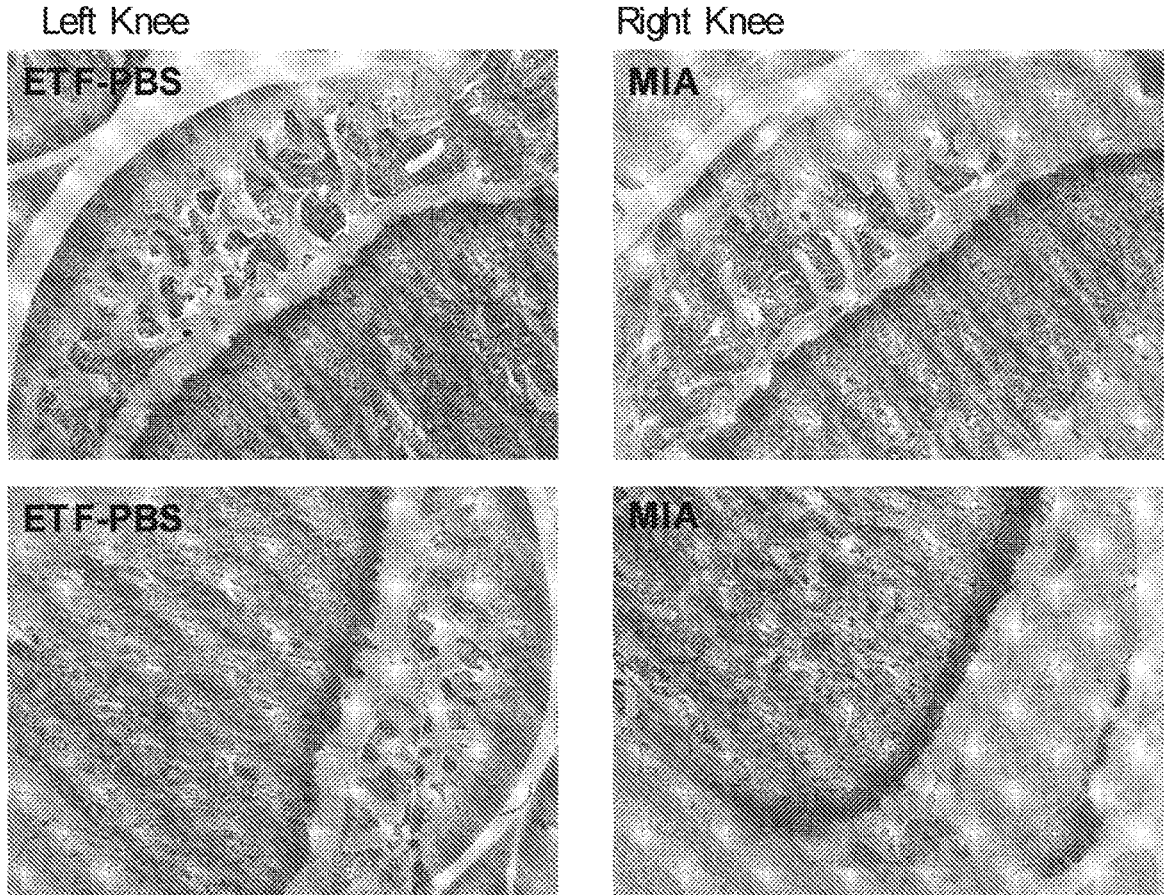

FIG. 36: Medial aspect of the rat knee stained with Safranin O Fast Green from animals treated with 3 mg/kg p75NTR-Fc from day 28 to day 56 following a low MIA or ETF-PBS injection on day 0 Into the knee (×4 magnification). Representative images are taken from animals treated with 3 mg/kg p75NTR-Fc. Each set of left and right knee image are taken from one individual animal to show the contralateral control.

Figure 37:
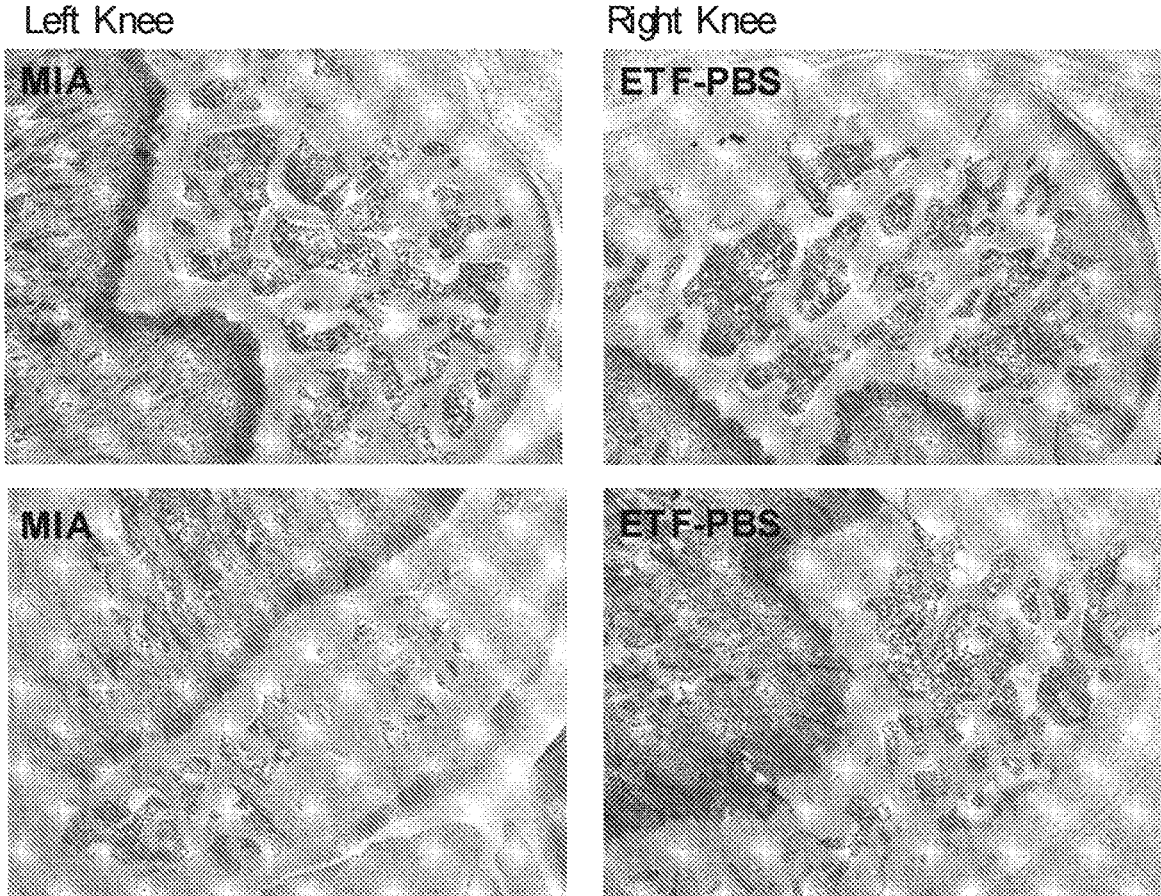

FIG. 37: Medial aspect of the rat knee stained with Safranin O Fast Green from animals treated with 1 mg/kg p75NTR-Fc from day 28 to day 56 following a low MIA or ETF-PBS injection on day 0 into the knee (×4 magnification). Representative images are taken from animals treated with 1 mg/p75NTR-Fc. Each set of left and right knee image are taken from one individual animal to show the contralateral control.

Figure 38:
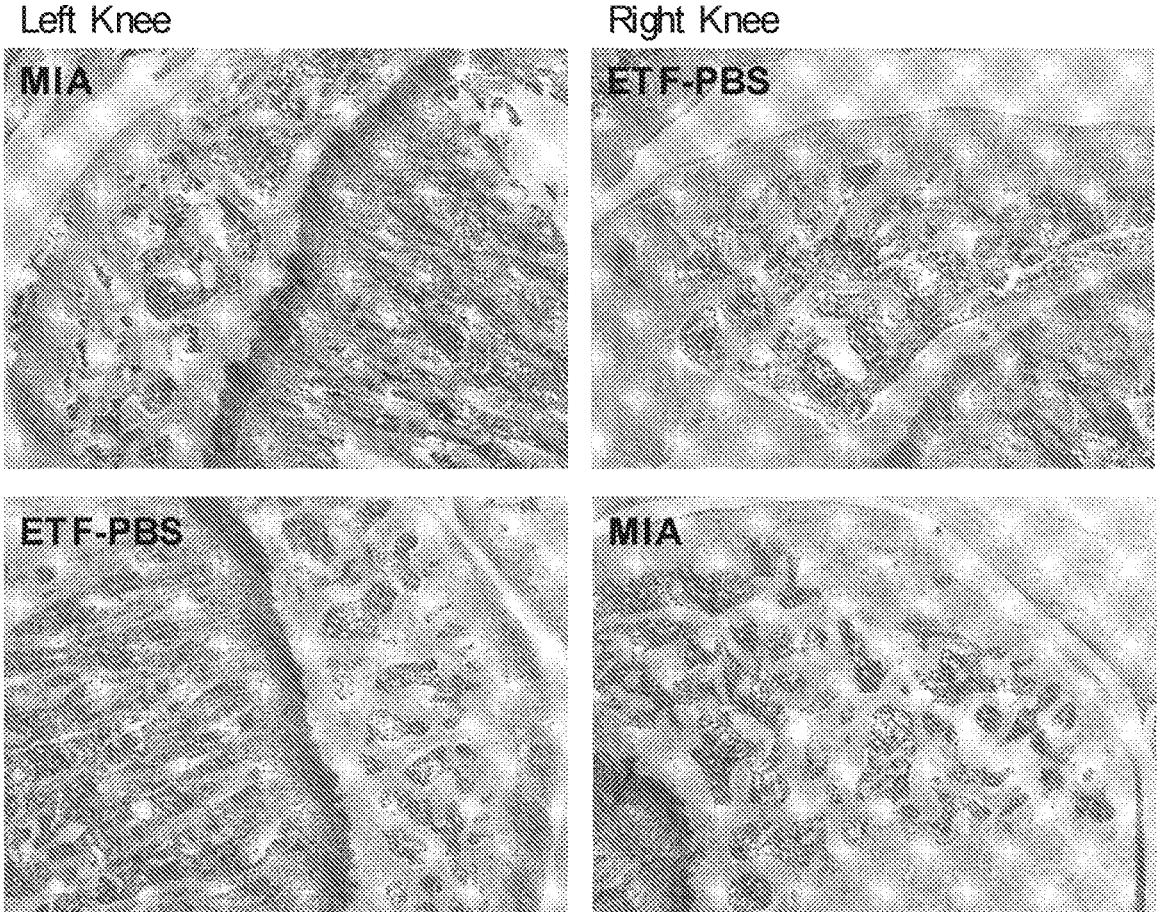

FIG. 38: Medial aspect of the rat knee stained with Safranin O Fast Green from animals treated with 0.3 mg/kg p75NTR-Fc from day 28 to day 56 following a low MIA or ETF-PBS injection on day 0 into the knee (×4 magnification). Representative images are taken from animals treated with 0.3 mg/kg p75NTR-Fc. Each set of left and right knee image are taken from one individual animal to show the contralateral control.

Figure 39:
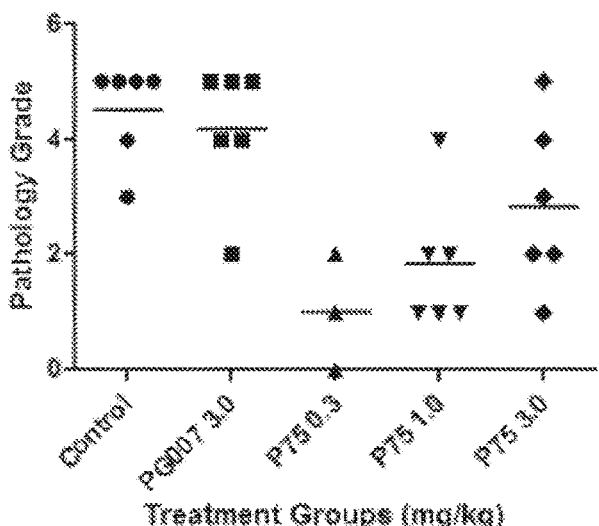

FIG. 39: Cartilage pathology grades. Administration of PG007 showed no histologically significant efficacy effects. P75NTR-Fc showed marked efficacy on chondroprotection at 0.3 and 1.0 mg/kg. The efficacy profile at 3.0 mg/kg was more variable—with 50% of the group showing overlay with the control group.

Figure 40:
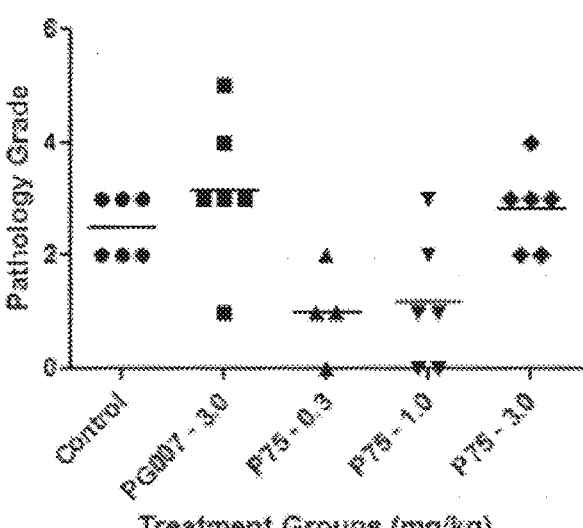

FIG. 40: Sub-chondral bone grades. Administration of PG007 was associated with histologically significant increase in sub-chondral bone pathology compared to the control group—similar to the profile observed with 3.0 mg/kg P75NTRFc. By contrast, administration of P75NTR-Fc at 0.3 and 1.0 mg/kg was associated with marked improvement in sub-chondral bone histology.

Figure 41:
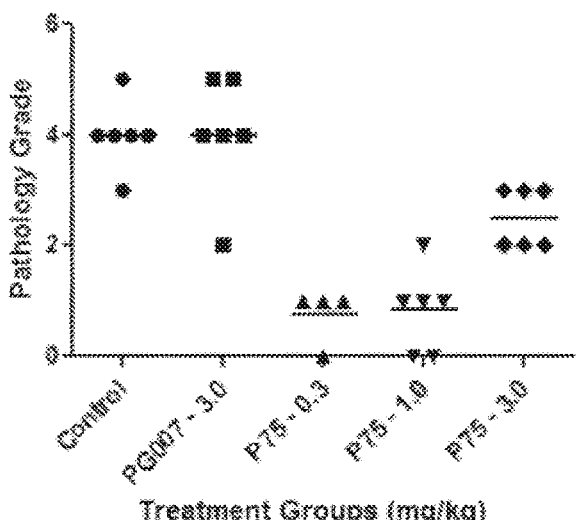

FIG. 41: Stromal cavity grades. Administration of PG007 was not associated with any histologically significant efficacy effects. By contrast, administration of P75NTR-Fc at all does was associated with reduction in osteolytic pathology and expansion of stromal cavities, although the effects at 0.3 and 1.0 mg/kg were most marked—both groups reducing pathology to almost normal levels.

Figure 42:
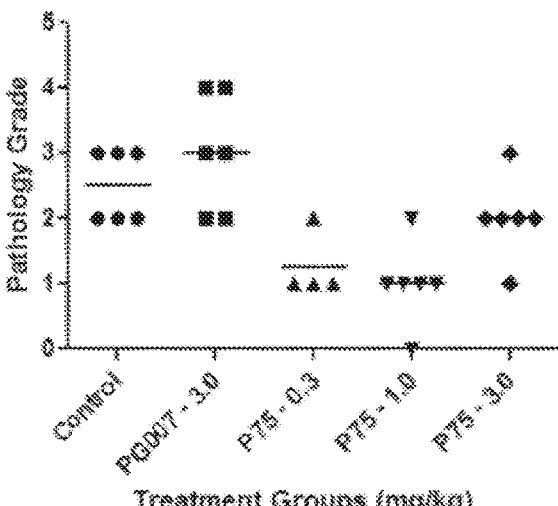

FIG. 42: Cancellous bone grades. Administration of PG007 was associated with cancellous bone pathology similar to controls—with two samples exceeding control ranges. By contrast, P75NTR-Fc markedly reduced cancellous bone pathology at the 0.3 and 1.0 mg/kg dose levels. P75NTF-Fc at 3.0 mg/kg presented a more variable profile, with the majority of samples showing overlay with the control group.

Figure 43:
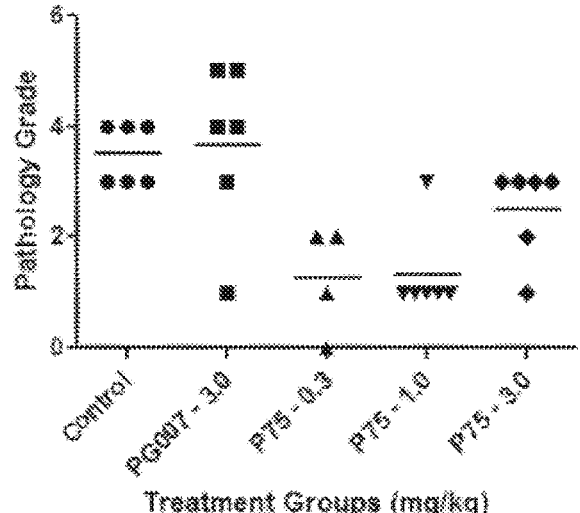

FIG. 43: Bone marrow hyper-cellularity. Administration of PG007 was associated with expansion of myeloid cells in the bone marrow, with four samples either at the top or exceeding the control range. P75NTR-Fc reduced marrow cellularity—with reduced myeloid expansion being a prominent feature—at the 0.3 and 1.0 mg/kg doses. The 3.0 mg/kg dose, although showing a trend towards inhibition, showed overlay with low level responders in the control group.

Figure 44:
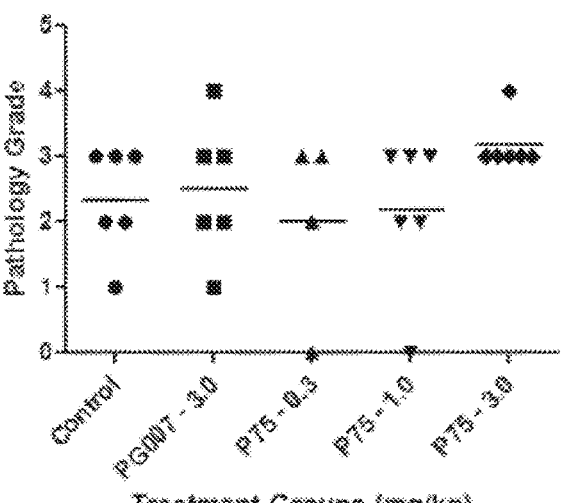

FIG. 44: Multi-focal bone sclerosis. There were no histologically significant differences between the study groups—although the P75NTR-Fc samples did show a clustering towards the top end of the control range.

Figure 45:
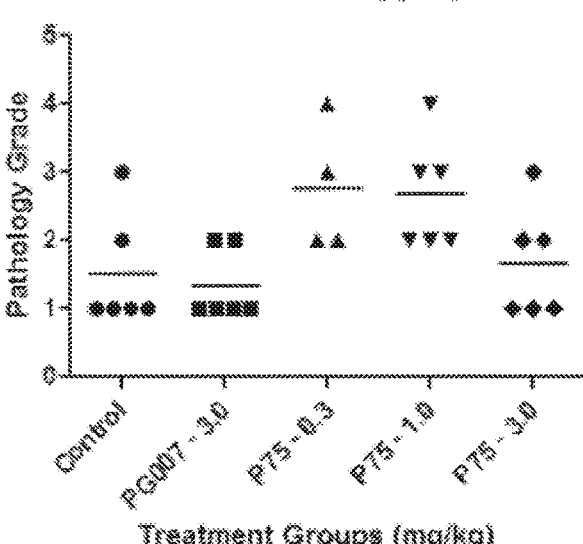

FIG. 45: Osteoblast hyperplasia. Administration of P75NTR-Fc at 0.3 and 1.0 mg/kg was associated with histologically significant osteoblast proliferation—with palisading and osteoblastic plate formation being especially prominent in the epiphyseal zone, at the sub-chondral bone/ cartilage zone. In addition, although not graded, there were prominent 'fibroblast-like' cells in this zone. PG007 and P75NTR-Fc (3.0 mg/kg) were histologically similar to controls (FIG. 45).

DETAILED DESCRIPTION

Osteoarthritis symptoms include inflammation, pain and swelling. In addition, the loss of cartilage can lead to the formation of bone outgrowths (osteophytes) which exacerbate symptoms and can lead to narrowing and distortion of the joint. Treatment options are currently limited to disease management options including physiotherapy, administration of pain killers and/or administration of anti-inflammatory drugs and, in some cases, joint replacement via surgery. Until now, no curative treatment options for osteoarthritis have been reported. There are also no reported treatments which halt progression of this degenerative disease. Accordingly, the present invention seeks to address the need for a curative osteoarthritis treatment, or at least to provide a treatment capable of halting degeneration in osteoarthritis.

Surprisingly, the present inventors have discovered that administration of a p75NTR neurotrophin binding protein (p75NTR(NBP)) in an accepted animal model of osteoarthritis not only halted disease progression, but also resulted in significant reversal of damage attributable to osteoarthritis progression.

Accordingly, there is provided in a first aspect a p75NTR neurotrophin binding protein (p75NTR(NBP)) for use in the treatment of osteoarthritis.

In preferred embodiments, the treatment of osteoarthritis includes relief from the symptoms of osteoarthritis. Preferably relief from the symptoms of osteoarthritis include, but are not limited to reduction in pain, inflammation, swelling, tenderness, joint stiffness or increase in joint mobility or any combination of these.

In a particularly preferred embodiment, treatment of osteoarthritis includes slowing or arresting of disease progression and/or reduction in cartilage loss. Preferably treatment of osteoarthritis includes reversal of disease progression, regrowth of cartilage and/or curative treatment. Preferably disease progression is determined by the rate of cartilage loss or regrowth. The rate of cartilage loss may be monitored by a variety of methods, including but not limited to Magnetic Resonance Imaging (MRI) or X-ray computed tomography (x-ray CT). In other preferred embodiments, disease progression may be monitored by determining the number of chondrocytes present in a joint.

The term "curative treatment" as used herein is Intended to encompass treatments which restore a patient to their pre-disease state. Such treatments may require continued administration of the active compound in order to maintain a pre-disease state. Alternatively, curative treatments may be halted once a pre-disease state is reached.

In other preferred embodiments, the treatment is of either primary or secondary osteoarthritis. Treatment of primary osteoarthritis includes treatment of both primary generalized nodal osteoarthritis and erosive osteoarthritis (EOA, also called inflammatory osteoarthritis).

Treatment of osteoarthritis is also intended to include amelioration of disease symptoms as classified under the WOMAC grading or Outerbridge classification systems. In preferred embodiments, the treatment of osteoarthritis results in reversal of disease progression, leading to a change of disease stage (WOMAC grading) or grade (Outerbridge classification).

In other preferred embodiments, the treatment of osteoarthritis includes prophylactic treatment.

In certain preferred embodiments the p75NTR(NBP) is a human p75NTR(NBP).

In other preferred embodiments the p75NTR(NBP) comprises a p75NTR(NBP) connected to one or more auxiliary molecules. Preferably, the one or more auxiliary molecules are selected from: (a) transferrin or a portion thereof; (b) albumin or a portion thereof; (c) an immunoglobulin Fc or a portion thereof; or (d) a polyethylene glycol polymer chain. In still other preferred embodiments the p75NTR (NBP) is connected to the one or more auxiliary molecules via one or more linkers. Preferably the linker is selected from: (a) a covalent bond; (b) a non-covalent bond; (c) a peptide bond; or (d) one amino acid or a plurality of amino acids comprising a peptide. In a particularly preferred embodiment, the p75NTR(NBP) comprises a p75NTR (NBP) connected to an immunoglobulin Fc or a portion thereof, optionally via a linker.

Where the p75NTR(NBP) is connected to more than one auxiliary molecule, optionally each auxiliary molecule is either the same or different or a mixture of the same and different. Similarly, where the p75NTR(NBP) is connected to more than one auxiliary molecule via one or more linkers, optionally each linker is either the same or different or a mixture of the same and different In an especially preferred embodiment the p75NTR(NBP) has the amino acid sequence according to SEQ ID NO 3.

In a particularly preferred embodiment the p75NTR (NBP) binds to any of NGF, BDNF, NT3 or NT4/5 with a binding affinity ($K_d$) of between about 5 pM to about 5 nM as measured by surface plasmon resonance at 20° C.

In a preferred embodiment the p75NTR(NBP) is for separate, sequential or simultaneous use in a combination combined with a second pharmacologically active compound. Preferably the second pharmacologically active compound of the combination is selected from an opioid analgesic, a nonsteroidal anti-inflammatory drug (NSAID), a barbiturate sedative, a benzodiazepine having a sedative action, an H1 antagonist having a sedative action, a sedative such as glutethimide, meprobamate, methaqualone or dichloralphenazone; a skeletal muscle relaxant; an NMDA receptor antagonist, an alpha-adrenergic, a tricyclic antidepressant, an anticonvulsant, a tachykinin (NK) antagonist, particularly an NK-3, NK-2 or NK-1 antagonist, a muscarinic antagonist, a COX-2 selective inhibitor, a coal-tar analgesic, in particular paracetamol; a neuroleptic a vanilloid receptor agonist or antagonist; a beta-adrenergic; a local anaesthetic; a corticosteroid; a 5-HT receptor agonist or antagonist; a 5-HT2A receptor antagonist; a cholinergic (nicotinic) analgesic; Tramadol®; a PDEV inhibitor; a cannabinoid; metabotropic glutamate subtype 1 receptor (mGluR1) antagonist; a serotonin reuptake inhibitor; a noradrenaline (norepinephrine) reuptake inhibitor; a dual serotonin-noradrenaline reuptake inhibitor; an inducible nitric oxide synthase (INOS) inhibitor; an acetylcholinesterase inhibitor; a prostaglandin E2 subtype 4 (EP4) antagonist; a leukotriene B4 antagonist; a 5-lipoxygenase inhibitor; a sodium channel blocker; or a 5-HT3 antagonist, and the pharmaceutically acceptable salts and solvates thereof.

Preferred opioid analgesics include, but are not limited to, morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine.

Preferred nonsteroidal anti-inflammatory drugs (NSAIDs) include, but are not limited to, aspirin, diclofenac, diflusinal, etodolac, fenbufen, fenoprofen, flufenisal, flurbiprofen, ibuprofen, Indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac.

Preferred barbiturate sedatives include, but are not limited to, amobarbital, aprobarbital, butabarbital, butabital, mephobarbital, metharbital, methohexital, pentobarbital, phenobartital, secobarbital, talbutal, theamylal or thiopental.

Preferred benzodiazepines having a sedative action include, but are not limited to, chlordiazepoxide, clorazepate, diazepam, flurazepam, lorazepam, oxazepam, temazepam or triazolam.

Preferred H1 antagonists having a sedative action include, but are not limited to, diphenhydramine, pyrilamine, promethazine, chlorpheniramine or chlorcyclizine.

Preferred sedatives include, but are not limited to, glutethimide, meprobamate, methaqualone or dichloralphenazone.

Preferred skeletal muscle relaxants include, but are not limited to, baclofen, carisoprodol, chlorzoxazone, cyclobenzaprine, methocarbamol or orphrenadine.

Preferred NMDA receptor antagonists include, but are not limited to, dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone.

Preferred alpha-adrenergics include, but are not limited to, doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline.

Preferred tricyclic antidepressants include, but are not limited to, desipramine, imipramine, amitriptyline or nortriptyline.

Preferred anticonvulsants include, but are not limited to, carbamazepine, lamotrigine, topiratmate or valproate.

Preferred tachykinin (NK) antagonists include, but are not limited to, (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl) phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S).

Preferred muscarinic antagonists include, but are not limited to, oxybutynin, tolterodine, propiverine, tropsium chloride, darifenacin, solifenacin, temiverine and ipratropium. Preferred COX-2 selective inhibitors include, but are not limited to, celecoxib, rofecoxib, parecoxib, valdecoxib, deracoxib, etoricoxib, or lumiracoxib.

Preferred coal-tar analgesics include, but are not limited to, paracetamol.

Preferred neuroleptics include, but are not limited to, droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan.

Preferred vanilloid receptor agonists include, but are not limited to, resinferatoxin. Preferred vanilloid receptor antagonists include, but are not limited to, capsazepine.

Preferred beta-adrenergics include, but are not limited to, propranolol. Preferred local anaesthetics include, but are not limited to, mexiletine. Preferred corticosteroids include, but are not limited to, dexamethasone.

Preferred 5-HT receptor agonists or antagonists, particularly 5-HT1B/1D agonists include, but are not limited to, eletriptan, sumatriptan, naratriptan, zolmitriptan or rizatriptan; Preferred 5-HT2A receptor antagonists include, but are not limited to, R(+)-alpha-(2,3-dimethoxy-phenyl)-1-[2-(4-fluorophenylethyl)]-4-piperidinemethanol (MDL-100907).

Preferred cholinergic (nicotinic) analgesics include, but are not limited to, ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine.

Preferred PDEV inhibitors include, but are not limited to, 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2′, 1′:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d] pyrimidin-7-one, 5-(5-acetyl-2-propoxy-3-pyridinyl)-3-ethyl-2-(1-isopropyl-3-azetidinyl)-2,6-dihydro-7H-pyrazolo [4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimldine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide.

Preferred cannabinoids include, but are not limited to, tetrahydrocannabinol, cannabinol, cannabidiol, cannabigerol, tetrahydrocannabivarin, cannabidivarin and cannabichromene.

Preferred serotonin reuptake inhibitors include, but are not limited to, sertrallne, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone.

Preferred noradrenaline (norepinephrine) reuptake inhibitors include, but are not limited to, maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine.

Preferred dual serotonin-noradrenaline reuptake inhibitors include, but are not limited to, venlafaxine, venlafaxine metabolite O-desmethylvenlafaxine, clomipramine, clomipramine metabolite desmethylclomipramine, duloxetine, milnacipran and imipramine.

Preferred inducible nitric oxide synthase (iNOS) inhibitors include, but are not limited to, S-[2-[(1-iminoethyl) amino]ethyl]-L-homocysteine, S-[2-[(1-iminoethyl)-amino] ethyl]-4,4-dioxo-L-cysteine, S-[2-[(1-iminoethyl)amino] ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thlo]-5-thlazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5- thiazolyl)butyl]thio]-5-chlorobenzonitrile, N-[4-[2-(3-chlorobenzylamino)ethyl]phenyl]thiophene-2-carboxamidine, or guanidinoethyldisulfide.

Preferred acetylcholinesterase inhibitors include, but are not limited to, donepezil. Preferred prostaglandin E2 subtype 4 (EP4) antagonists include, but are not limited to, N-[({2-[4-(2-ethyl-4,6-dimethyl-1H-imidazo[4,5-c]pyridin-1-yl)phenyl]ethyl}amino)-carbonyl]-4-methylbenzene-sulfonamide or 4-[(1S)-1-({[5-chloro-2-(3-fluorophenoxy) pyridin-3-yl]carbonyl}amino)ethyl]benzoic acid.

Preferred leukotriene B4 antagonists include, but are not limited to, 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870.

Preferred 5-lipoxygenase inhibitors include, but are not limited to, zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

Preferred sodium channel blockers include, but are not limited to, lidocaine. Preferred 5-HT3 antagonists include, but are not limited to, ondansetron.

Preferably the p75NTR(NBP) is formulated for oral, sublingual, buccal, topical, rectal, inhalation, transdermal, subcutaneous, intravenous, intra-arterial, intramuscular, Intracardlac, Intraosseous, Intrasynovial, intradermal, Intraperitoneal, transmucosal, vaginal, intravitreal, intra-articular, peri-articular, local or epicutaneous administration.

In a further aspect of the present invention there is provided a nucleic acid encoding a p75NTR(NBP), for use in the treatment of osteoarthritis as defined above.

In another aspect of the present invention there is provided a replicable expression vector for transfecting a cell, comprising a nucleic acid encoding a p75NTR(NBP), for use in the treatment of osteoarthritis as defined above.

In yet another aspect of the present invention there is provided a host cell expressing a p75NTR(NBP), for use in the treatment of osteoarthritis as defined above.

In a still further aspect of the present invention there is provided a pharmaceutical composition, comprising the p75NTR(NBP), the nucleic acid molecule, the replicable expression vector, or the host cell described above, and a pharmaceutically acceptable carrier and/or an excipient.

Preferred pharmaceutically acceptable carriers include, but are not limited to, [ . . . ]

Another aspect of the invention pertains to a kit comprising:

a. the p75NTR(NBP), the nucleic add molecule, the replicable expression vector, the host cell, or the pharmaceutical composition described above; and b. instructions for the administration of an effective amount of the p75NTR(NBP), nucleic acid molecule, replicable expression vector or pharmaceutical composition to an individual for any one or more of the prevention or treatment of osteoarthritis and/or a symptom of osteoarthritis or for ameliorating, controlling, reducing incidence of, or delaying or reversing the development or progression of osteoarthritis and/or a symptom of osteoarthritis.

In another aspect of the present invention there is provided a method of treating and/or preventing osteoarthritis and/or a symptom of osteoarthritis in an individual comprising administering to said individual a therapeutically effective amount of the p75NTR(NBP), the nucleic acid molecule, the replicable expression vector, the host cell, or the pharmaceutical composition described above, optionally further comprising a pharmaceutically acceptable carrier.

EXAMPLES

Example 1—Affinity Measurements of p75NTR Using Biacore

Methods

The kinetics and affinity of p75NTR are determined by surface plasmon resonance technology using a Biacore T200 (GE Healthcare, Sweden). The Biacore methods are based on those recommended by Abdiche and colleagues. (Abdiche, et al., 2008) Protein A (10 μg/mL in 10 mM sodium acetate buffer) is immobilised on the surface of a CM5 biosensor chip by the amine coupling method using 1-ethyl-3-(3-dimethylaminopropyl carbodiimide) (EDC) and N-hydroxy-succinimide (NHS) and ethanolamine as provided in the amine coupling kit.

Briefly, the steps involved in the amine-coupling immobilisation wizard on the Biacore instrument are:

EDC and NHS are mixed 1:1

EDC/NHS mixture is injected over each flow cell of a CM5 chip for 420 seconds at 10 μL/min Protein A [10 μg/mL] in 10 mM sodium acetate buffer, pH 4.5 is injected over the same flow cell for 420 seconds at 10 μL/min Ethanolamine is injected over the same flow cell for 420 seconds at 10 μL/min Approximately 2200-2900 response units (RU) are immobilised. One flow cell is set as the blank control. p75NTR-Fc is captured onto the other flow cell of the biosensor chip at 15° C. using a 30 second injection of p75NTR (10 μg/mL in HBS-EP [0.01 M HEPES pH 7.4, 0.15 M NaCl, 3 mM EDTA, 0.005% v/v Surfactant P20]) at a flow rate of 10 μL/min to achieve the desired p75NTR RU level (~400 RU; calculated using the molecular weights of the p75NTR, the relevant neurotrophin and stoichiometric ratio). Immobilising p75NTR rather than the ligand helps ensure the neurotrophins are in their native states.

A single-cycle kinetics study is performed by injecting increasing concentrations of neurotrophin in HBS-EP buffer over the flow cells for 120 seconds at 30 μL/min per neurotrophin concentration. Following the final neurotrophin injection HBS-EP is flowed over the chip for 600 seconds to determine dissociation rates. Chip sensor surfaces are regenerated back to their Protein A surface by injecting 10 mM Glycine HCl, pH 2 for 60 seconds at 30 μL/min prior to every new injection cycle.

Multi-cycle kinetics studies are performed by injecting the lowest neurotrophin concentration over the flow cells for 300 seconds at 30 μL/min, followed by HBS-EP buffer for 300 seconds at 30 μL/min. The chip is then regenerated by 2×60 second injections of 10 mM Glycine, HCl pH 2 and the cycle repeated for each increasing neurotrophin concentration.

Results p75NTR binds reversibly to the neurotrophins NGF, BDNF, NT-3 and NT-4. The affinities measured using Biacore are given in Table 1.

TABLE 1

| Affinity of p75NTR for the four neurotrophins | | |
|---|---|---|
| Neurotrophin | Affinity (pM) | Affinity Range(pM) |
| NGF | 554 | 50-5000 |
| BDNF | 41.8 | 5-500 |

TABLE 1-continued

| Affinity of p75NTR for the four neurotrophins | | |
|---|---|---|
| Neurotrophin | Affinity (pM) | Affinity Range(pM) |
| NT-3 | 14.2 | 1-100 |
| NT-4 | 181 | 10-1000 |

Example 2—Monoiodoacetate-Induced Osteoarthitis Study

Experimental osteoarthritis induced by intra-articular injection of monoiodoactetate (MIA) In the rear knee of rats is a well-recognised model of osteoarthritis. The pathological progression of the disease and pain behaviour have been reported (Guzman, et al., 2003) (Fernihough, et al., 2004). MIA disrupts glycolysis by inhibition of glyceraldehyde-3-phosphate dehydrogenase, leading to chondrocyte death (Harvey & Dickenson, 2009). The structural integrity of cartilage relies on the normal functioning of chondrocytes, thus MIA-induced loss of chondrocytes leads to cartilage degeneration and changes of the subchondral bone consistent with the clinical histopathology of OA (Janusz, et al., 2001; Kobayashi, et al., 2003; Naveen, et al., 2014). Injection of 0.3 mg MIA induces loss of cartilage over a 10-week period. Cartilage loss is greatest between Week 3 and Week 6 (FIG. 1).

44 male Wistar rats (Charles River, UK) housed in pairs and weighing 200-250 g on Day −2, are randomly assigned by pair to treatment such that the mean body weight of each treatment group is similar. On Day 0 the rats receive treatment as indicated in Table 1. Freshly prepared human IgG (3.25 mg/mL in endotoxin free phosphate buffered saline [ETF-PBS]) and p75NTR (3.25 mg/mL in EF-PBS) are administered subcutaneously. The laboratory personnel are blinded to the treatment of the animals throughout the study.

TABLE 2

| Treatment groups. MIA, monoiodiacetate; IgG, immunoglobulin G | | |
|---|---|---|
| Treatment group (n) | MIA | Antibody |
| 1 (6) | 0.3 mg | Human IgG 3.0 mg/kg |
| 2 (6) | 0.3 mg | p75NTR 0.3 mg/kg |
| 3 (6) | 0.3 mg | p75NTR 1.0 mg/kg |
| 4 (6) | 0.3 mg | p75NTR 3.0 mg/kg |

Three hours later all animals are anaesthetised with isofluorane. Each anaesthetised animal receives an intra-articular injection of 50 μL EF-PBS containing 0.3 mg MIA in either the right or left knee, according to the randomisation schedule. The contralateral knee of each anaesthetised animal is injected with 50 μL EF-PBS. A further respective antibody or p75NTR treatment is administered on Day 5 and 15.

The study terminates on Day 26, when cartilage loss is evident and active (FIG. 1). Animals are anaesthetised using isofluorane, terminal blood samples are taken by cardiac puncture and plasma samples prepared. The skin on the lower hind legs is removed and the muscle bundles separated from the bones but left intact with the knee. The femur, fibula and tibia are severed and the knee with attached muscle is placed in 10% neutral buffered formalin. Tissue samples are kept in buffered formalin for 48-72 hours before processing for histological analysis.

Tissue samples are prepared for light microscopy using standard procedures as soon as possible after collection to minimise damage caused from the formalin fixation. The samples are decalcified in 8% formic acid for 10 days, processed using a Shandon Citadel tissue processer and embedded into molten paraffin wax. At least four sections (10 μm) from each rat knee tissue block are processed for standard Haematoxylin and Eosin (H&E) staining using an automated linear staining machine (Leica ST4040). Further sections are stained using Safranin O. Slides are viewed at either times four or ten magnification and image analysis is performed using a computerised system. The total cartilage area, from cartilage surface down to the border between the calcified cartilage and subchondral bone is measured. Light absorption of stain bound to tissue sections is quantified under monochromatic light with digital densitometry. The intensity of the red staining of the glycosaminoglycans by Safranin O is quantitated by measuring the cartilage area stained when the absorption threshold is set at 130 nm.

Figure 2:
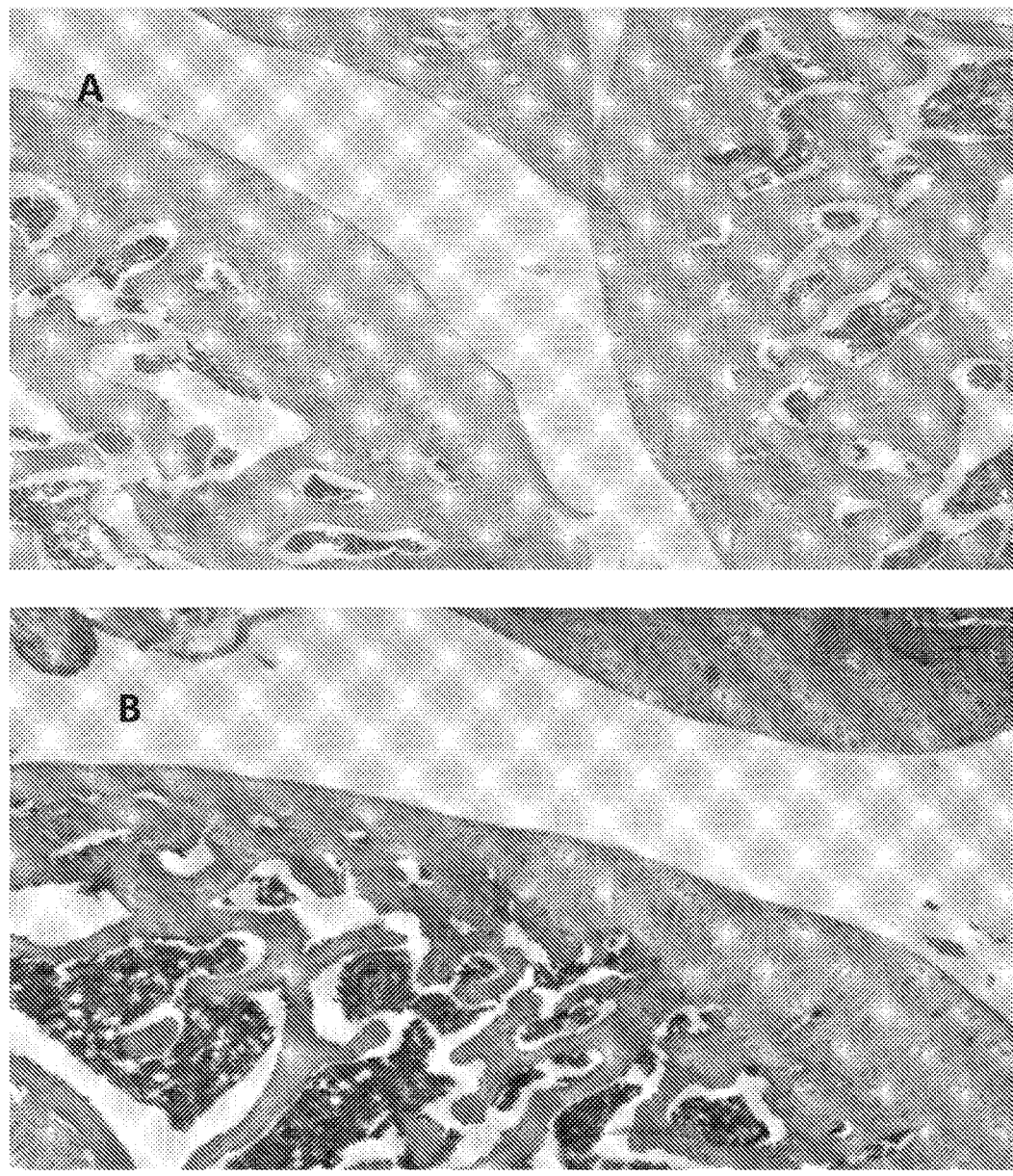
FIG. 2: Medial aspect of the rat knee stained with haematoxylin and eosin from animals treated with control antibody (A,B) or p75NTR 0.3 mg/kg (C,D), 1 mg/kg (E,F), 3 mg/kg (G,H). Experimental osteoarthritis was induced in the left knee (A,C,E,G) of each animal by intra-articular injection of MIA. The right knee was injected with ETF-PBS (control; B,D,F,H). (×4 magnification) Each set of left and right knee images are taken from an individual animal to show the contralateral control.
Figure 2:
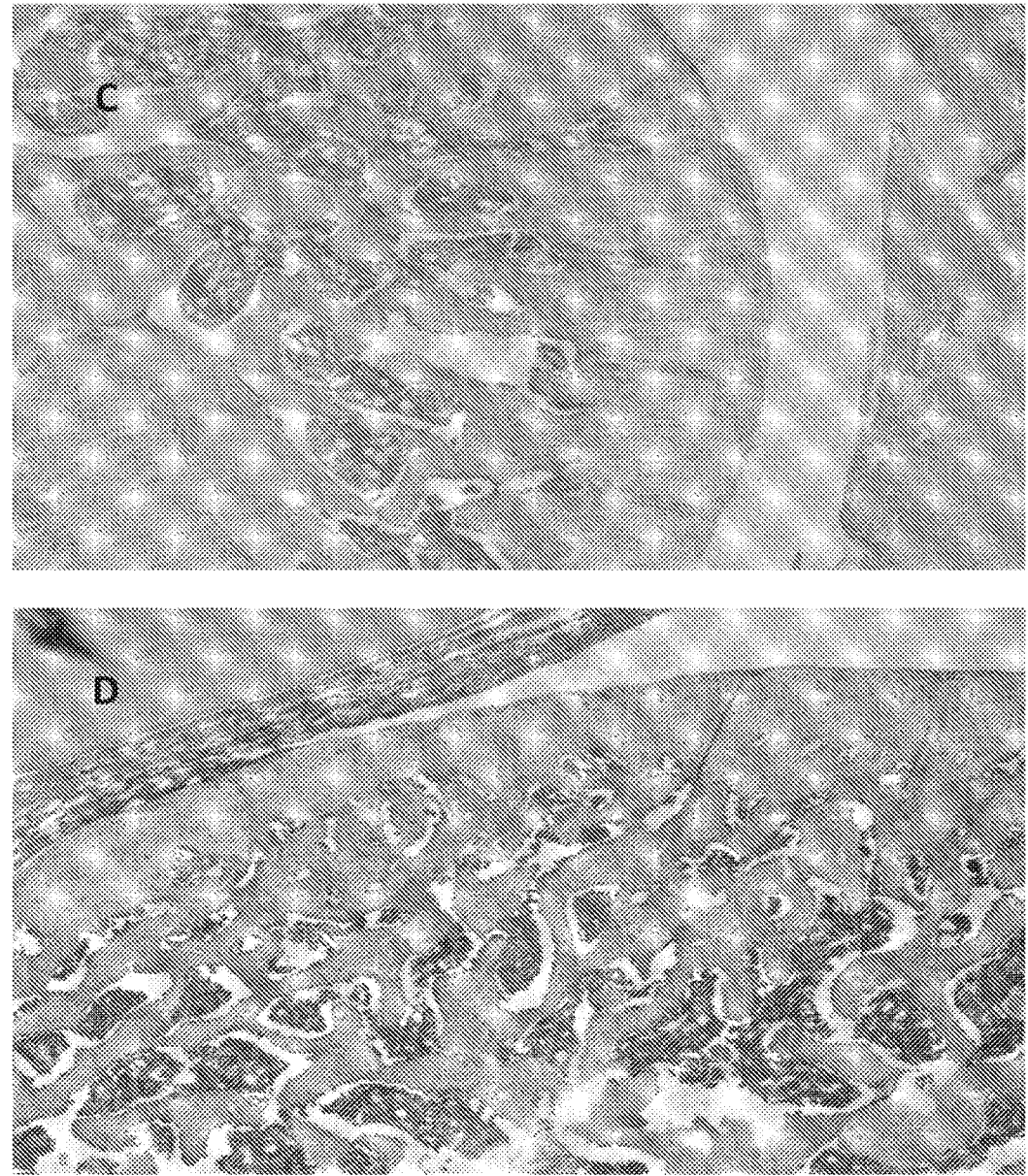
Figure 2:
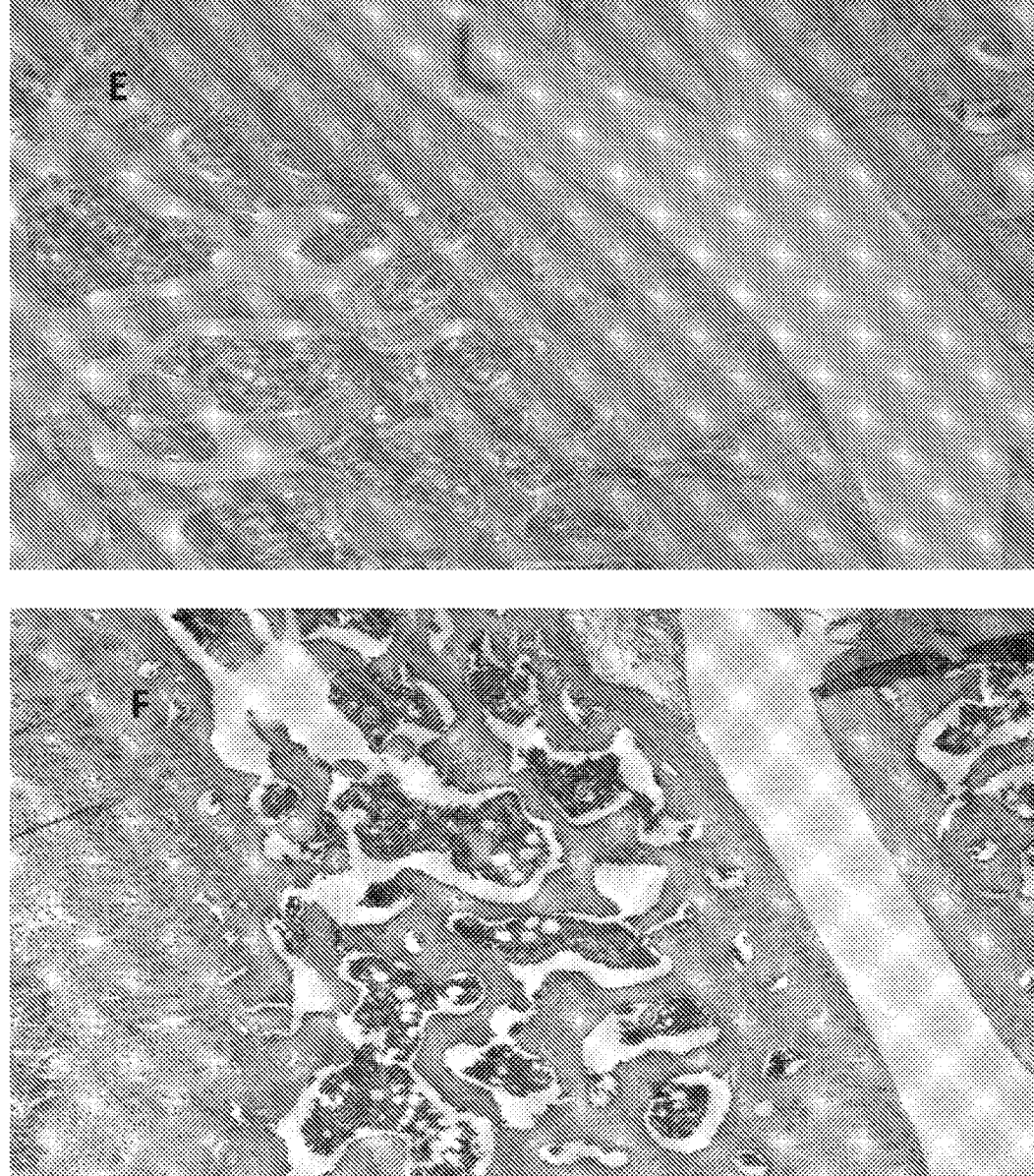
Figure 2:
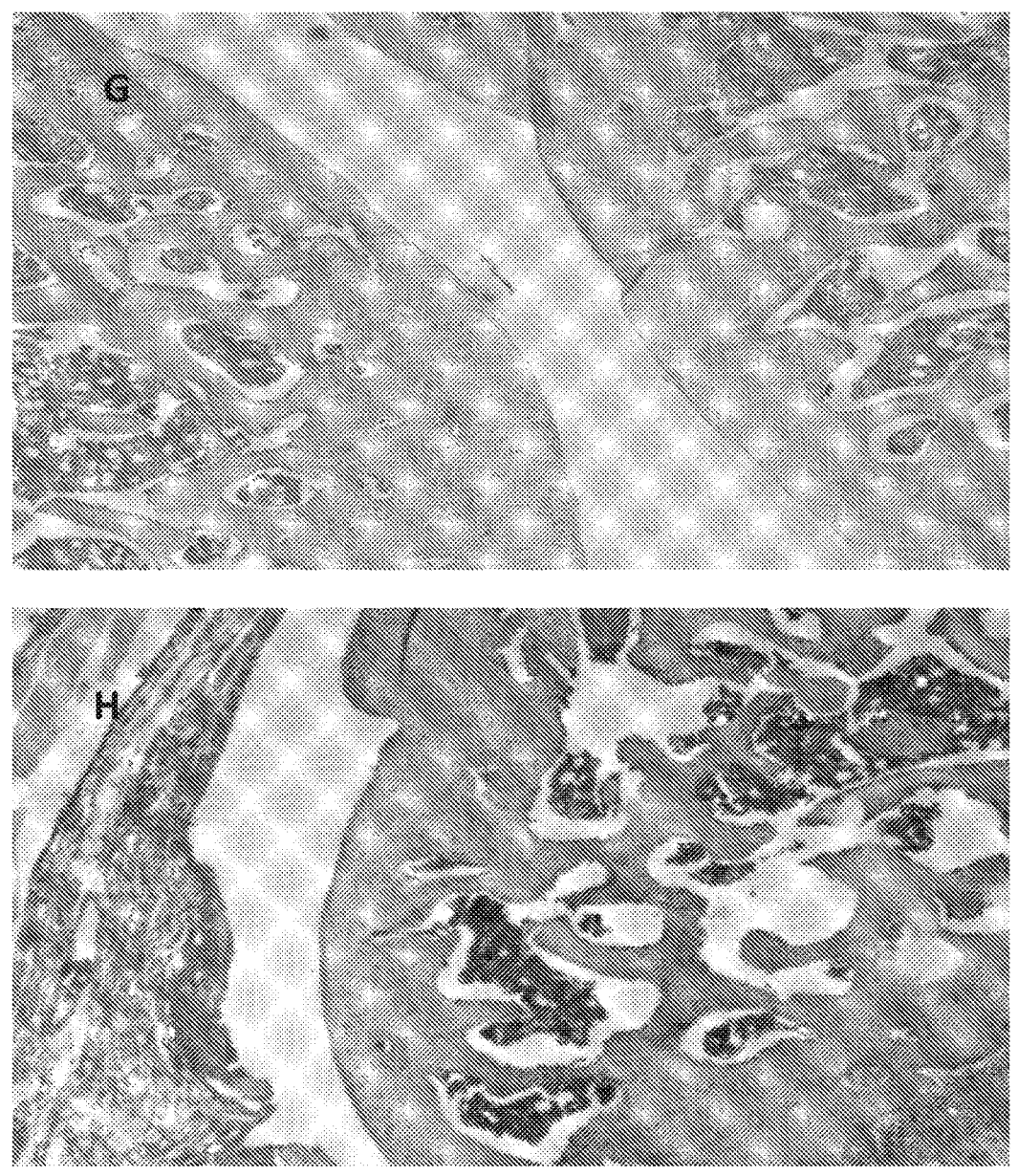
Figure 3:
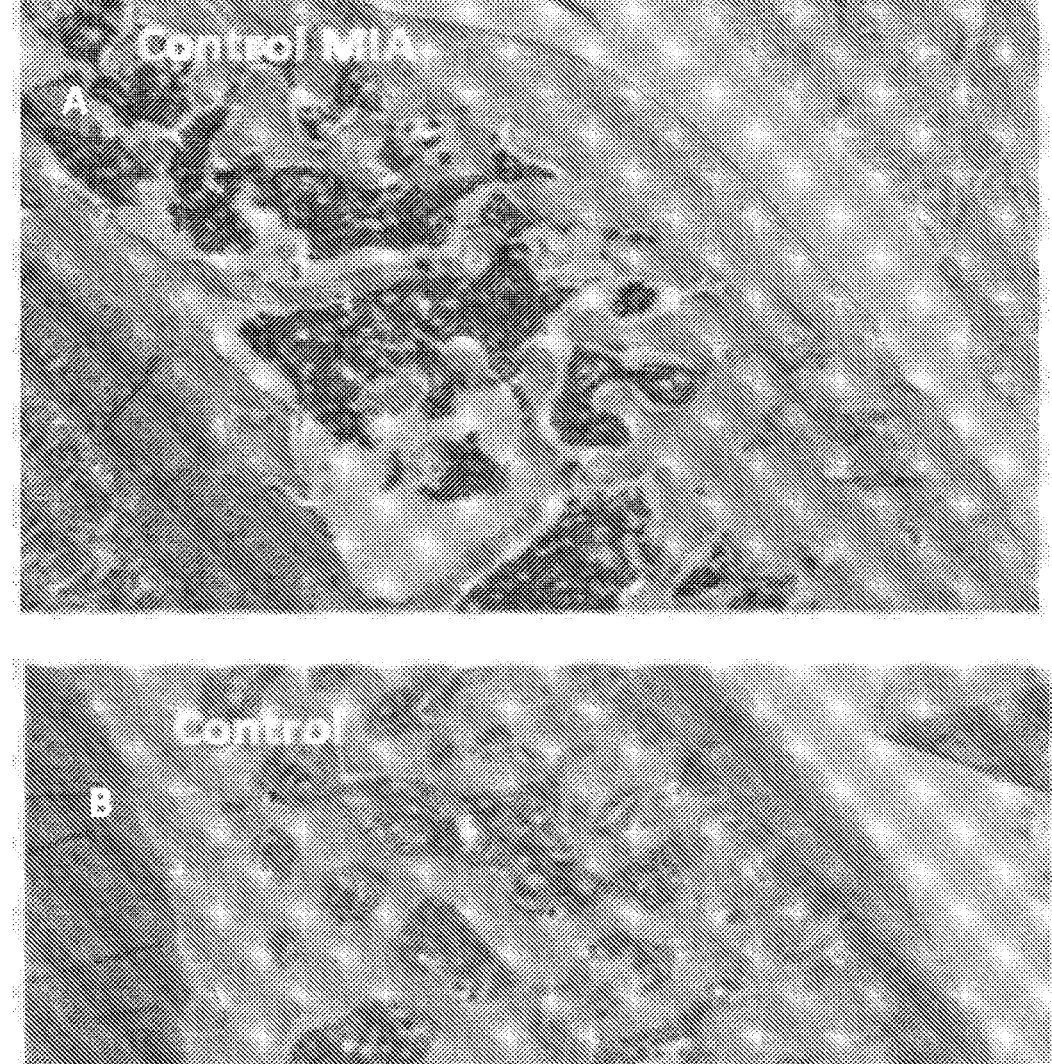
FIG. 3: Medial aspect of the rat knee stained with safranin O from animals treated with control antibody (A,B) or p75NTR 3 mg/kg (C,D). Experimental osteoarthritis was induced in the left knee (A and C) of each animal by intra-articular injection of MIA. The right knee was injected with ETF-PBS (control; B and D). (×4 magnification) Each set of left and right knee images are taken from an individual animal to show the contralateral control

The concentration of control antibody and exogenous p75NTR in plasma is estimated by measuring human IgG using an enzyme—linked immunosorbent assay (ELISA). Results—Effect of p75NTR on Histological Changes in the Knee Following MIA-Induced OA No tissue degeneration nor features of OA were observed in knees that had been injected with ETF-PBS in animals from all treatment groups (FIG. 2B,D,F,H, FIG. 3B,D,F,H). In contrast, MIA-injected knees in animals treated with control antibody showed areas of mild chondrocyte degeneration, which frequently involved the entire thickness of the articular cartilage (FIG. 2A). There was evidence of a recent inflammatory response in some areas, marked by leukocyte accumulation. Treatment with p75NTR did not accelerate the progression of OA (FIG. 2C,E,G). There were fewer histological changes in the architecture of low MIA treated knees treated with p75NTR compared with animals treated with control antibodies, indicating protection from injury or repair of damage. This was evident at all p75NTR concentrations tested (0.3-3.0 mg/kg). Indeed, animals treated with the highest dose of p75NTR-Fc had significant (P<0.05) increase in cartilage area (evidence of p75NTR-Fc induced repair in OA see FIG. 4).

Effect of p75NTR on Proteoglycan Density in the Knee Following MIA-Induced OA

Figure 4:
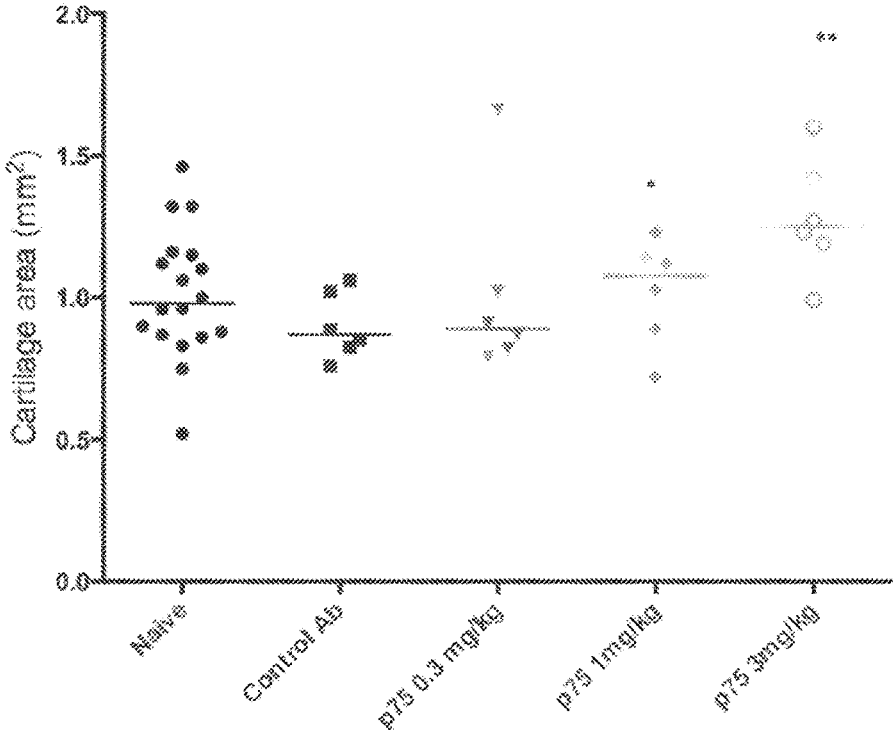
FIG. 4: Total cartilage area (from cartilage surface down to the border between the calcified cartilage and subchondral bone) in rear knee joints on Day 26. Significant difference compared to control antibody are denoted thus *P<0.1 and **P<0.05.

The overall cartilage area in MIA-treated knees was improved in animals treated with p75NTR-Fc: this was significantly different (P<0.05) for animals treated with p75NTR-Fc at 3.0 mg/kg compared to corresponding control animals on Day 26 post intra-articular injection (FIG. 4).

Figure 5:
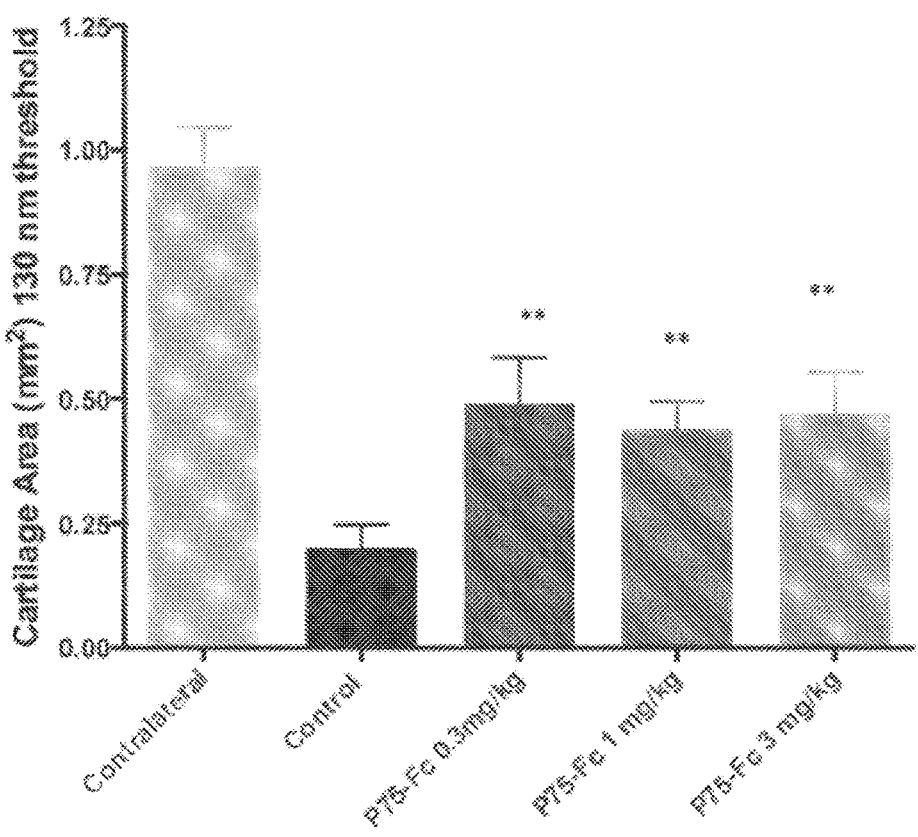
FIG. 5: Cartilage area stained by safranin O at threshold absorption wavelength of 130 nm in rear knee joints following 26 days of treatment. Data are mean ± SEM, n=6 Significant difference compared to control antibody are denoted thus **P<0.05.

The intensity of safranin O staining, as assessed by image analysis, which is proportional to the glycosaminoglycan content of cartilage, showed marked differences (P<0.05) between the treatment groups (see FIG. 5). Using an absorption threshold of 130 nm, only 20% of the cartilage from MIA-treated knee was red-stained above the 130 nm threshold in animals treated with control antibodies compared with the contralateral knees, indicating a substantial loss of glycosaminoglycans. In contrast, approximately 50% of the cartilage in the MIA-treated knees of animals receiving p75NTR-Fc was above the 130 nm threshold (FIG. 5). This indicates that p75NTR-Fc is preventing the ongoing loss of structural integrity of the cartilage following MIA injection and moreover disease modification in OA.

Example 3—Effects of p75NTR-Fc on Regression of Osteoarthritis in Rat Compared to PG-007

The aim of this study is to assess whether ascending doses of p75NTR-Fc can cause regression of OA once the disease has been established. In addition the efficacy of the treatment in terms of the pain associated with MIA induced arthritis in the rat has been assessed and compared with treatment with the Tanezumab like anti-Neurotrophin Growth Factor (NGF) antibody, PG-007.

Protocol

Reagents

TABLE 3

| Details of reagents used in Example 3 | | |
| --- | --- | --- |
| Reagent | Source and catalogue number | Batch number |
| Monosodium Iodoacetate (MIA) | Sigma I2512 | #SLBB6147V |
| Endotoxin free PBS (ETF-PBS) | Promocell C-40240 | 359P109 |
| 10% neutral buffered formalin solution | Sigma HT501320 | 090M4370 |
| EDTA (dipotassium salt dihydrate) | Sigma ED2P | BCBF9021V |

Preparation of MIA

MIA was prepared at a concentration of 0.3 mg/50 μl ETF-PBS (the volume used for each intra-articular injection) which is equivalent to 6 mg/ml MIA stock solution. 68 mg of MIA was weighed out and dissolved in 11.3 ml ETF-PBS. The MIA was prepared a day in advance and was stored at 4° C. in the dark until required. All animals received the MIA prepared from the same batch.

Test Agents

TABLE 4

| Details of test agents used in Example 3 | | |
| --- | --- | --- |
| Test agent | Source and catalogue number | Batch number |
| PG-007 0.026 EU/mg | Lonza at 3.25 mg/ml, Batch 1 (provided by Levicept) | |
| p75NTR-Fc Human IgG Fc fragment full-length protein | 2.90 mg/ml stock AbCam AB90285 prepared at 2.15 mg/ml in ETF-PBS | GR196868-1 |

Preparation of Test Agents

The test agents used in this study were prepared fresh on the specific day that the animals were dosed (see Table 4). Wherever possible the volumes of each antibody prepared were equal so that the in vivo scientist injecting the antibody was unaware of what treatment was in each vial (see Table 5).

TABLE 5

| | | Stock | Stock | Vehicle | Final | Final | Dose |
|---|---|---|---|---|---|---|---|
| | Dose | Concentration | volume | volume | volume | concentration | volume |
| Antibody | (mg/kg) | (mg/ml) | (ml) | (ml) | (ml) | (mg/ml) | (ml/kg) |
| | | | Typical preparation of test agents used in Example 3 | | | | |
| PG-007 | 3 | 3.25 | 3.30 | 14.70 | 18 | 0.60 | 5 |
| p75NTR-Fc | 3 | 2.90 | 3.73 | 14.27 | 18 | 0.60 | 5 |
| p75NTR-Fc | 1 | 2.90 | 1.24 | 16.76 | 18 | 0.20 | 5 |
| p75NTR-Fc | 0.3 | 2.90 | 0.37 | 17.63 | 18 | 0.06 | 5 |
| IgG-Fc | 3 | 2.15 | 5.00 | 13.00 | 18 | 0.60 | 5 |

Animals 39 male Wistar rats (from Charles River, UK) weighing 120-150 g on arrival were used in Example 3. Each animal was checked on arrival and appeared outwardly healthy. They were randomly assigned to a cage of three and each rat was allocated a unique identification number by a tattoo on the tail. Animals were acclimatised to the animal unit for at least ten days prior to the start of the study on day 0.

Once the rats had acclimatised to their environment they were transferred to a stock/procedure room, where all the in vivo procedures were carried out. Animals were kept illuminated by fluorescent lights set to give a 12 hour light-dark cycle (on 07.00 off 19.00) as recommended in the Home Office Animals (Scientific Procedures) Act 1986. The rooms were air-conditioned and the air temperature (21° C.+/−2° C.) and relative humidity were routinely measured.

Rats were fed R105-25 irradiated complete diet for rats (Scientific Animal Food and Engineering, Augy, France) and autoclaved water was available ad libitum. Each batch of diet was checked and screened routinely for composition and contaminants. Nesting and cages were autoclaved and each cage was individually ventilated (IVC system).

Experimental Design

Following the induction of arthritis by the intraarticular injection of MIA in one knee and once were significant differences were observed in the weight bearing (incapacitance measurements) of the limbs treated with MIA compared to its contralateral control limb treated with ETF-PBS, animals were randomised into five treatment groups of equivalent nociceptive behaviour (n=6 animals per group) and one vehicle control group (n=3). Six naïve animals were included as negative controls.

TABLE 6

| Intra-articular injection in one knee (n) | Treatment (group) by the subcutaneous route | Treatment days | Terminal day |
|---|---|---|---|
| | | Overview of experimental design for Example 3 | |
| MIA 0.3 mg (6) | PG-007 3 mg/kg | 30, 35, 39, 45 and 50 | 58 |
| MIA 0.3 mg (6) | P75NTR-Fc 0.3 mg/kg | 30, 35, 39, 45 and 50 | 58 |
| MIA 0.3 mg (6) | P75NTR-Fc 1 mg/kg | 30, 35, 39, 45 and 50 | 58 |
| MIA 0.3 mg (6) | P75NTR-Fc 3 mg/kg | 30, 35, 39, 45 and 50 | 58 |
| MIA 0.3 mg (6) | Human IgG FC fragment full length protein | 30, 35, 39, 45 and 50 | 58 |
| MIA 0.3 mg (3) | PBS | 30, 35, 39, 45 and 50 | 58 |
| Naïve (6) | None | None | 58 |

Body weight was regularly recorded through the study and assessment of spontaneous pain was measured at weekly intervals.

As anti NGF anti-neurotrophins have been shown to cause rats to scratch around the face and neck, animals were regularly observed for signs of skin lesions and any lesion scores recorded, particularly after day six, to ensure that we were not reaching the humane clinical end-point as determined in previous studies (animals will be killed if the maximum area of total skin lesions exceeds 10 cm² or if any one lesion was greater than 2 cm×3 cm in size and became deeper and wet with no signs of healing within a 24 hour period).

On the terminal day a blood sample was taken by cardiac puncture and plasma prepared. The knees were removed and placed in 10% neutral buffered formal saline and processed for histology.

Randomisation of Treatment(s)

Injection of MIA

Randomisation was carried out so that either the left or right knee of each rat was injected with MIA (with the contralateral knee from each rat injected with ETF-PBS). The allocation of which knee received MIA or saline for each rat was produced using a random number generator in Microsoft Excel for the Mac (Version 14.1.1). Personnel who had no contact with the animals carried out the randomisation procedure and allocation (see Appendix 1 for the schedule). Two 7 ml polypropylene vials were labelled for each animal to denote the left or right knee (total of 66 vials). Two people (one scoring and checking to the master randomisation sheet and one aliquoting the solution for the intra-articular injection) prepared the 66 vials. The aliquoting was carried out in sequence so that the MIA vials were filled first followed with the remaining vials being filled with ETF-PBS (this was the contralateral knee vial for each animal). The vials for the naïve animals were left empty.

Dosing of Test Agents

Animals were randomised into treatment groups of equal differences in the nociceptive behaviour of the knee that had been treated with MIA compared to the knee treated with vehicle control. This was performed on day 28 following the induction of OA.

Animal Procedures

Intra-Articular Injection of the Knee

Rats were anaesthetised by inhalation of Isoflurane using a Boyles Apparatus. The hairs on both knees of each animal were clipped and the knees swabbed with ethanol. Each knee was injected through the infra-patellar ligament with 50 µl of either 0.3 mg MIA in ETF-PBS or ETF-PBS alone using a 0.5 ml sterile Becton Dickinson Micro-Fine insulin syringe with an attached 27 G needle. The six naïve animals were anaesthetised and the hairs on both knees were dipped only. Throughout the study in vivo scientists were blind to the treatment status of all animals.

Dosing of Test Agents

Test agents were dosed by the subcutaneous route in the scruff of the neck or flank using a dose volume of 5 ml/kg.

Assessment of Spontaneous Pain

Spontaneous pain was determined for each animal at weekly intervals by measuring the weight bearing of the left and right hind limbs using an incapacitance tester (Linton Instruments, U.K.). Rats were placed in an appropriately sized perspex animal box on the incapacitance tester so that their hind feet sat on separate sensors. The size of the box chosen was based on the body weight of the rat (small rat holder for rats up to 450 g and large rat/guinea pig holder for rats over 450 g), which allowed the rat to sit comfortably without being squashed, but similarly did not offer too much space so that the rat could turn around. Once the rat was steady and calm, the weight bearing of each limb was recorded over 5 seconds and the average force in grams exerted by both hind limbs was recorded. The weight distribution of the hind paws was determined five times for each rat at each time point, and the mean of the five readings calculated. The individual weight bearing data was converted into a weight distribution by dividing the weight of the right limb by the total weight for both hind limbs.

Terminal Blood Sample

Terminal blood samples were taken by cardiac puncture under Isoflurane anaesthetic with a Terumo 2 ml syringe and 21 G needle that had been flushed with 1% potassium EDTA in MilliQ water. The blood collected was put into 2 ml polypropylene tubes. Animals were then killed by cervical dislocation.

Plasma Preparation

Terminal blood samples were centrifuged at 2700×g for 10 minutes and the plasma aliquoted into polypropylene tubes (four aliquots per animal) and frozen at –80° C.

Removal of the Rat Knees

The skin on the lower leg was removed and the muscle bundles separated from the bones but left intact with the knee. The femur, fibula and tibia were severed and the knee with attached muscle was removed and placed in approximately 80 ml of 10% neutral buffered formalin in a 125 ml screw cap container. The knees were kept in buffered formalin from 48 to 72 hours before being processed for histological analysis.

Processing for Histology

Tissue samples were prepared for light microscopy using standard procedures and carried out externally at the University of Cambridge veterinary school. Briefly, after the knee joints were fixed, the tissues were rinsed with PBS and subsequently decalcified in 8% formic acid for 10 days. Following decalcification the tissue was processed using a Shandon Citadel tissue processer which dehydrated the tissue through a series of graded ethanol concentrations (six changes of 4 hour ranging from 75% to 100% ethanol), rinsed with 100% chloroform (three changes of 4 hour) and finally embedded into molten paraffin wax to form a tissue block (two changes of 4 hour). The tissues were embedded into cassettes using a Surgipath PEC 3001 machine with molten paraffin wax. The tissue was processed as soon as possible after collection to minimise damage caused from the formalin fixation so that tissue sections could be potentially used for immunohistochemistry.

At least four 10 μm sections were cut from each rat knee tissue block using a Leica RM2135 wax microtome. Two sections were placed on a glass slide and the slides were processed for standard Haematoxylin and Eosin (H&E) and Safranin O fast Green (Safranin O F/G) staining using an automated linear staining machine (Leica ST4040). Briefly, the linear staining machine has 23 reagent stations and four water stations arranged in a configuration for staining slides, which follow a standard H&E or Safranin O F/G protocol. For H&E slides were exchanged between the 27 stations after one minute in each and follow a xylene, ethanol, water, haematoxylin, water, acid alcohol, water, eosin, water, ethanol and xylene series. (all solvents from Fisher Scientific and H&E from Leica). The sections were allowed to air dry, were mounted and covered with a coverslip ready to be viewed under a microscope.

Image Analysis

Slides were viewed at either times 2, 4 or 10× magnification using an Olympus AX70 microscope using Image-Pro Plus image analysis software (suite v7.0, Media Cybernetics, U.K.). An initial informal analysis of the stained tissue sections for OA-like features was performed to show the overall gross changes of the medial knee joint of each rat.

Image analysis was conducted on the SO/FG slides using the X2 objective where the total area of the cartilage (in $mm^2$) was determined for all the rat knees (MIA and ETF-PBS treated knees). The depth of the cartilage layer (a minimum of 6 measurements was made per medial knee joint) and this was compared to the depth of the subchondral bone from the same knee joint.

Data Analysis

Image analysis (such as cartilage area) and pain assessment data (for example, weight distribution imbalance) was analysed for each animal using classical statistics. Multiple measurements were collected and averaged from animals treated with either p75-NTR-Fc (at different doses) or PG-007 and values were compared to control animals using the appropriate classical statistical tests. For all analyses, $p<0.05$ was taken to indicate statistical significance.

Results

Body Weight

The body weights of the rats in the different groups were compared to test for differences in the sizes of the animals. At day 0, there was no statistically significant difference between the body weights of the animals in the different treatment groups ($p=0.76$ n.s., one-way ANOVA, see FIG. 30).

The mean body weight between the six treatment groups (rats treated with p75NTR-Fc or PG-007 compared to rats treated with control antibody) was not statistically significant from each other during the course of the study ($p=n.s.$, two way ANOVA, see FIG. 31).

Spontaneous Pain Measurements

Effects of p75NTR-Fc and PG-007 on the Spontaneous Pain Provoked by OA

Spontaneous pain was assessed using an incapacitance tester to measure the distribution of weight through the rear limbs. Assessments were made at baseline (except for group 7, naïve animals) and again on days 15, 21 and 28 following the injection of MIA into one knee (contralateral knees were injected with ETF-PBS). The data is shown in FIG. 32 and is illustrated as the proportion of the total weight over the rear limbs that are being supported by the MIA-treated rear limb. For naïve animals the proportion of weight that is passing through the left rear limb is shown.

For all the animals there was no statistically significant difference between the proportion of weight on the treated rear limb and the theoretical expectation of 0.5 (even distribution across both rear limbs at baseline on day 0 ($p=0.379$, Kruskal Wallis test; see FIG. 32). By day 28, all five treatment groups were significantly different to the theoretical mean of 0.5 and were essentially taking the weight of their MIA injected knee (see FIG. 32). Based on previous studies this indicated that the extent of OA pathology was significant enough to start dosing the rats.

Dosing was started in rats with the respective treatment regimen from day 30 onwards until the end of the study on day 56 (treatment every 5 days via the subcutaneous route). During the course of the study further assessment of spontaneous pain were measured (made on days 35, 42, 49 and 56, see FIG. 4). Throughout the study up until day 49, animals treated with control IgG Fc remained significantly different between the proportion of weight on the treated rear limb and the theoretical expectation of 0.5, indicating that the MIA treated knee was causing pain to the animal (see FIG. 33). In contrast, in animals treated with anti-NGF PG-007 and those treated with p75NTR-Fc (from 0.3 to 3 mg/kg) there was no significant between the proportion of weight on the MIA treated rear limb and the theoretical expectation of 0.5 (ie even distribution of weight on the rear limbs) as time progressed.

Histological Changes in the Knee Following Mia-Induced Oa

Effects of p75NTR-Fc and PG007 on the Regression of OA

Knees injected with MIA from animals treated with control antibodies showed areas of chondrocyte degeneration, which in some areas has led to full cartilage loss (FIG. 34). This is highlighted by the associated loss of Safranin O fast green staining in the cartilage. In addition, there were significant pathological changes in the sub chondral bone underlying the areas of the greatest cartilage damage (FIG. 34). There is a spectrum of changes in the subchondral bone, which reflect both reactive changes and progression driven from remodelling through to sclerotic changes (FIG. 34).

Animals treated with 3 mg/kg PG-007 for 28 days after significant pathology has been established (identified by a pain assessment where the proportion of weight on the treated rear limb and the theoretical expectation of 0.5 were significantly different) showed significant histological changes compared to animals treated with control antibody with loss of the overall integrity of the rat knee and no histological evidence of efficacy (FIG. 35). This pathology is consistent with associated loss of cartilage and bone marrow and evidence of bone necrosis, which overall leads to an overall rapid progression and in some animals a worsening of the OA compared to animals treated with control antibodies (FIG. 35). In contrast, animals treated with p75NTR-Fc (0.3 to 3 mg/kg) exhibit a very different histopathology and there is evidence of significant chondroprotection and an associated significant increase in subchondral bone pathology compared to animals treated with control antibodies, which leads to an overall reduced severity of the bone pathology and OA (FIGS. 36-38). This is phenotypically represented by a reduced myeloid expansion in the bone marrow, which diminishes the inflammatory mediated osteolytic drive.

Animals treated with the lower doses of p75NTR-Fc (0.3 and 1 mg/kg) show the most marked changes in the histopathology (see FIGS. 37 and 38), and in both treatment groups the pathology was almost at normal levels. Taking into consideration the histological results at 3 mg/kg p75NTR-Fc (see FIG. 36) the overall profile suggests that p75NTR-Fc exhibits a "bell-shaped" dose response curve.

Histopathology Assessment

Histopathology was performed on Safranin O Fast Green stained sections of decalcified knees. In general, the quality of both tissue processing and staining was excellent, with only three slides rejected on quality grounds. The slides were organised into treatment groups and so the initial pathology assessment was not blinded. However, for the purposes of grading, all groups (with the exception of vehicle) were randomised—using a simple random number sequence—in order to reduce observer bias and diagnostic drift.

Descriptive Cartilage Histopathology Phenotypes

Control Group

There was a clear distinction between paired slides. Slides with most marked cartilage pathology are: 4RA, 5LA, 6LB, 10RA, 11LB (insufficient cartilage to grade on slide 11RA) and 12RB. The majority of cartilage changes were full thickness erosions with obvious peripheral chondrocyte necrosis.

Group 4—PG007, 3 mg/kg

There was a clear distinction between paired slides. Slides with most marked cartilage pathology are: 1RA, 2RB, 3LB, 34LA, 35LA, 36RB. Overall, the cartilage pathology was histologically similar to the control group.

Group 3—P75NTR-Fc, 0.3 mg/kg

The distinction between paired slides was not so marked compared to the control group. Administration of P75NTR-Fc was associated with marked inhibition of MIA-induced cartilage pathology—indeed near normal in two cases. Three slides were rejected from this group on quality grounds.

Group 1—P75NTR-Fc, 1.0 mg/kg

The distinction between paired slides was not so marked compared to the control group. Slides with most marked cartilage pathology (although modest compared to control lesions) are: 7LA, 8LA, 13RB, 15RA, 31RB, 33LB. Administration of P75NTR-Fc was associated with marked inhibition of MIA-induced cartilage pathology.

Group 2—P75NTR-Fc, 3.0 mg/kg

This group presented with marked variability in terms of efficacy effects on cartilage pathology—with a spectrum of effects from control-type lesions to those resembling Group 1 (50%). Slides with the most marked cartilage pathology are: 16LB, 17RA, 18RB, 22RB, 23LA and 24LA. Administration of P75NTR-Fc at the top dose did not show the unequivocal effects associated with 0.3 and 1.0 mg/kg.

Histopathology Grade Criteria

Allocation of grade is based upon the most frequent lesion observed within each anatomical zone. Based upon the initial assessment, key histological features were identified in the control group and which showed evident changes following 1.0 mg/kg P75NTR-Fc administration. Grade criteria were those which have been employed in previous MIA study pathology assessment (MLF).

Cartilage Pathology

Many publications detail the use of the Mankin Score for grading human cartilage pathology. The original Mankin Score (or HHGS score) ranges from 0 (normal) to 14 (severe pathology) and suffers from marked inter-observer bias. In addition, this scoring system underestimates the involvement of pannus pathology and often conflates early changes with normal variation. Importantly, the Mankin Score expands the grade range for moderate to severe pathology, and markedly conflates mild to moderate changes. Thus, the Mankin Score, applied directly, has questionable utility in pre-clinical studies as it rarely describes a pharmacodynamic range and is insensitive to the differences in cell turnover between rodents and man. The grading system used in this study is a modification of the OARSI system using the descriptive scheme of Pelletier:

0—no significant abnormalities; 1—minimal superficial fibrillation; 2—superficial erosion; loss of superficial zone chondrocytes; 3—deep zone erosion; 4—full thickness erosion; multi-focal exposure of sub-chondral bone, <50% area; 5—loss of cartilage plate; detritic forms in articular space, >50% area Sub-Chondral Bone The sub-chondral bone plate reacts to loss of cartilage integrity across the spectrum of cartilage grades before undergoing degenerative changes—essentially osteolysis mediated. 0—no significant abnormalities; 1—superficial zone disorganisation (erratic osteoid zones); 2—full thickness disorganisation; 3—multi-focal osteolysis; 4—multi-focal osteopenia; 5—confluent osteopaenic zones Stromal Cavities The stromal cavities are the marrow cavities within and immediately distal to the subchondral plate. 0—no significant abnormalities; 1—minimal osteolysis; 2—moderate osteolysis; 3—marked osteolysis with evidence of multiple lytic pits in majority of cavities; 4—post-osteolytic fusion of cavities; 5—fused cavities breach sub-chondral bone and/or periosteum Cancellous Bone The cancellous bone system undergoes reactive changes in minimal cartilage pathology due to changes in joint blomechanics—progressing to a more degenerative phenotype secondary to inflammation 0—no significant abnormalities; 1—multi-focal areas of superficial bone resorption/osteolysis; 2—multiple areas of marked osteolysis; 3—multiple areas of osteolysis with loss of normal tide-mark zonation; 4—multi-focal zones of osteolysis with evident osteocyte loss; 5—cancellous bone breach with/without bone fusion Bone Marrow Hyper-Cellularity 0—no significant abnormalities; 1—multiple focal condensed foci of cells within marrow stroma; 2—multiple focal condensed foci of cells within marrow stroma and periosteal pits; 3—diffuse marrow hyper-cellularity—zonal; 4—expansion of bone marrow into stromal cavities; 5—breach of marrow compartment into sub-chondral plate or periosteal with/without pannus mixing Bone Sclerosis Bone sclerosis is usually seen as areas of fibroplastic expansion from the stromal cavities. 0—no significant abnormalities; 1—occasional, small, foci; 2—multiple foci; 3—multiple confluent foci; 4—multiple confluent foci with associated bone degeneration; 5—multiple confluent foci with bone cysts Osteoblast Hyperplasia 0—no significant abnormalities; 1—multiple osteoblast plates; 2—multiple hypertrophic osteoblast plates; 3—obvious osteoblast palisading; 4—hypertrophic osteoblast plates—zonal; 5—hypertrophic osteoblast plates—multi-zonal.

Histology Grade Results (Most Severe Cartilage Pathology Sample from Paired Sets Plotted)

Cartilage Pathology

Administration of PG007 showed no histologically significant efficacy effects. P75NTR-Fc showed marked efficacy on chondroprotection at 0.3 and 1.0 mg/kg. The efficacy profile at 3.0 mg/kg was more variable—with 50% of the group showing overlay with the control group (FIG. 39).

Sub-Chondral Bone

Administration of PG007 was associated with histologically significant increase in sub-chondral bone pathology compared to the control group—similar to the profile observed with 3.0 mg/kg P75NTRFc. By contrast, administration of P75NTR-Fc at 0.3 and 1.0 mg/kg was associated with marked improvement in sub-chondral bone histology (FIG. 40).

Stromal Cavities

Administration of PG007 was not associated with any histologically significant efficacy effects. By contrast, administration of P75NTR-Fc at all does was associated with reduction in osteolytic pathology and expansion of stromal cavities, although the effects at 0.3 and 1.0 mg/kg were most marked—both groups reducing pathology to almost normal levels (FIG. 41).

Cancellous Bone

Administration of PG007 was associated with cancellous bone pathology similar to controls—with two samples exceeding control ranges. By contrast, P75NTR-Fc markedly reduced cancellous bone pathology at the 0.3 and 1.0 mg/kg dose levels. P75NTF-Fc at 3.0 mg/kg presented a more variable profile, with the majority of samples showing overlay with the control group (FIG. 42).

Bone Marrow Hyper-Cellularity

Administration of PG007 was associated with expansion of myeloid cells in the bone marrow, with four samples either at the top or exceeding the control range. P75NTR-Fc reduced marrow cellularity—with reduced myeloid expansion being a prominent feature—at the 0.3 and 1.0 mg/kg doses. The 3.0 mg/kg dose, although showing a trend towards inhibition, showed overlay with low level responders in the control group (FIG. 43).

Bone Sclerosis

There were no histologically significant differences between the study groups—although the P75NTR-Fc samples did show a clustering towards the top end of the control range (FIG. 44).

Osteoblast Hyperplasia

Administration of P75NTR-Fc at 0.3 and 1.0 mg/kg was associated with histologically significant osteoblast proliferation—with palisading and osteoblastic plate formation being especially prominent in the epiphyseal zone, at the sub-chondral bone/cartilage zone. In addition, although not graded, there were prominent 'fibroblast-like' cells in this zone. PG007 and P75NTR-Fc (3.0 mg/kg) were histologically similar to controls (FIG. 45).

Adverse Effects

Two rats treated with 3 mg/kg PG-007 developed skin lesions. Very minor skin lesions began to appear around the face, neck and shoulder region in some rats by day 45 (15 days following treatment) but became more apparent from day 49 (19 days following treatment) onwards in one rat. These lesions were not associated with the injection site. Rats were checked regularly and the number, size and extent of each lesion was quantified to ensure we remained within the humane clinical end-point of the study. No rats treated with p75NTR-Fc at any concentration developed skin lesions.

DISCUSSION

Histopathology

PG007 was not associated with histological evidence of efficacy. In contrast, P75NTR-Fc at 0.3 and 1.0 mg/kg was associated with histologically significant chondroprotection, with reduced severity of bone pathology and osteolysis-mediated bone erosion. The finding of reduced bone marrow hyper-cellularity (notably myeloid expansion) supports this phenotype, and suggests that limitation of an inflammation-mediated osteolytic drive is involved in the efficacy response. Importantly, these doses were also associated with an expansion of the osteoblast pool—suggestive that the mechanism of efficacy of P75NTR-Fc is a dual mechanism, limiting osteolysis (thus limitation of myeloid cell activation) whilst expanding the osteoblast pool (thus augmenting the mesenchyme cell pool). The histological profile of the 3.0 mg/kg P75NTR-Fc group suggests that P75NTR-Fc exhibits a 'bellshaped' dose response curve. Although in many respects the histological profile of 3.0 mg/kg P75NTR-Fc and PG007 are similar, the exact phenotype suggests that the osteolytic drive of P75NTRFc is less than that of PG007 on a dose equivalency basis. Classically, histopathology assessment of MIA models is based upon a linear relationship from primary cartilage pathology resulting in reactive bone changes. The bone marrow changes are often deemed consequential, secondary to a reactive synovitis arising from biomechanical changes due to cartilage loss. There is accumulating data from osteoimmunology suggesting that this linear relationship is naïve, and that the bone compartment can exert an important role in conditioning both the temporal development and phenotype of the cartilage response. Indeed, this research supports imaging data from human studies which show bone remodelling even in minimal grade cartilage lesions. Thus it is likely that the cartilage and sub-chondral bone should be viewed as an integrated functional unit—with the latter providing conditioning to support chondrocyte proliferation and survival and so influencing structural outcomes in osteoarthritis. The data from the present study offers support to the hypothesis that manipulation of the NGF pathway, whilst offering possibilities for reducing osteolysis, also may augment mesenchyme cell mediated osteoprotection—and thus suppressing the drive from superficial chondronecrosis to deep zone lesions and hence full thickness cartilage erosions and cartilage loss.

CONCLUSIONS

In this study the effect of a therapeutic dosing regimen using p75NTR-Fc (from 0.3 to 3 mg/kg) was investigated to determine whether regression of the OA pathology following MIA injection could be observed. OA was allowed to develop for 30 days before dosing commenced, which was identified by pain measurements being significantly different from the theoretical mean of 0.5.

Animals treated with lower doses of p75NTR-Fc (0.3 and 1 mg/kg) were both analgesic and efficacious and showed significantly less OA pathology compared to animals treated with control antibodies. In contrast, despite rats treated with 3 mg/kg PG-007 showing analgesia this was not associated with histological evidence of efficacy and any improvement in the OA pathology. Animals treated with the higher dose of p75NTR-Fc (3 mg/kg) were analgesic however; there were some histopathological similarities to animals treated with 3 mg/kg PG-007.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A pharmaceutical composition, comprising an amount of the polypeptide of SEQ ID NO: 3 and a pharmaceutically acceptable carrier, an excipient, or a combination thereof, wherein the amount is an amount effective to treat osteoarthritis or to slow, arrest, or reverse progression of osteoarthritis in a mammalian subject suffering therefrom, and wherein the amount comprises a dose of between 0.3-3.0 mg/kg body weight.

2. The pharmaceutical composition of claim 1, wherein to treat osteoarthritis comprises:

a. reduction in cartilage loss;

b. regrowth of cartilage;

C. increase in joint mobility;

d. curative treatment; or e. any combination thereof.

3. The pharmaceutical composition of claim 2, wherein progression of osteoarthritis is determined by the rate of cartilage loss or regrowth.

4. The pharmaceutical composition of claim 1, wherein the polypeptide of SEQ ID NO:3 binds to any of nerve growth factor (NGF), brain-derived neurotrophic factor (BDNF), neurotrophin-3 (NT3) or neurotrophin 4/5 (NT4/5) with a binding affinity (Kd) of 5 pM to 5 nM as measured by surface plasmon resonance at 20° C.

5. The pharmaceutical composition of claim 1, wherein the polypeptide of SEQ ID NO:3 is formulated for oral, sublingual, buccal, topical, rectal, inhalation, transdermal, subcutaneous, intravenous, intra-arterial, intramuscular, intracardiac, intraosseous, intrasynovial, intradermal, intraperitoneal, transmucosal, vaginal, intravitreal, intra-articular, peri-articular, local or epicutaneous administration.

6. The pharmaceutical composition of claim 1, wherein the amount comprises a dose of between 0.3-1.0 mg/kg body weight.

* * * * *

SEQUENCE LISTING

```
<160> NUMBER OF SEQ ID NOS: 32

<210> SEQ ID NO 1
<211> LENGTH: 460
<212> TYPE: PRT
<213> ORGANISM: Artificial Sequence
<220> FEATURE:
<223> OTHER INFORMATION: Fusion Protein

<400> SEQUENCE: 1

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
            115                 120                 125
```

-continued

```
Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
                180                 185                 190

Gln Asp Leu Ile Ala Ser Thr Val Ala Gly Val Val Thr Thr Val Met
            195                 200                 205

Gly Ser Ser Gln Pro Val Val Thr Arg Gly Thr Thr Asp Asn Asp Ile
    210                 215                 220

Glu Gly Arg Met Asp Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460
```

```
<210> SEQ ID NO 2
<211> LENGTH: 462
<212> TYPE: PRT
<213> ORGANISM: Artificial Sequence
<220> FEATURE:
<223> OTHER INFORMATION: Fusion Protein

<400> SEQUENCE: 2
```

```
Met Glu Trp Ser Trp Val Phe Leu Phe Phe Leu Ser Val Thr Thr Gly
1               5                   10                  15

Val His Ser Lys Glu Ala Cys Pro Thr Gly Leu Tyr Thr His Ser Gly
            20                  25                  30
```

-continued

```
Glu Cys Cys Lys Ala Cys Asn Leu Gly Glu Gly Val Ala Gln Pro Cys
        35                  40                  45

Gly Ala Asn Gln Thr Val Cys Glu Pro Cys Leu Asp Ser Val Thr Phe
    50                  55                  60

Ser Asp Val Val Ser Ala Thr Glu Pro Cys Lys Pro Cys Thr Glu Cys
65                  70                  75                  80

Val Gly Leu Gln Ser Met Ser Ala Pro Cys Val Glu Ala Asp Asp Ala
                85                  90                  95

Val Cys Arg Cys Ala Tyr Gly Tyr Tyr Gln Asp Glu Thr Thr Gly Arg
            100                 105                 110

Cys Glu Ala Cys Arg Val Cys Glu Ala Gly Ser Gly Leu Val Phe Ser
        115                 120                 125

Cys Gln Asp Lys Gln Asn Thr Val Cys Glu Glu Cys Pro Asp Gly Thr
    130                 135                 140

Tyr Ser Asp Glu Ala Asn His Val Asp Pro Cys Leu Pro Cys Thr Val
145                 150                 155                 160

Cys Glu Asp Thr Glu Arg Gln Leu Arg Glu Cys Thr Arg Trp Ala Asp
            165                 170                 175

Ala Glu Cys Glu Glu Ile Pro Gly Arg Trp Ile Thr Arg Ser Thr Pro
            180                 185                 190

Pro Glu Gly Ser Asp Ser Thr Ala Pro Ser Thr Gln Glu Pro Glu Ala
            195                 200                 205

Pro Pro Glu Gln Asp Leu Ile Ala Ser Thr Val Ala Gly Val Val Thr
    210                 215                 220

Thr Val Met Gly Gly Gly Glu Pro Lys Ser Ser Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly
```

-continued

```
          450             455             460

<210> SEQ ID NO 3
<211> LENGTH: 443
<212> TYPE: PRT
<213> ORGANISM: Artificial Sequence
<220> FEATURE:
<223> OTHER INFORMATION: Fusion protein

<400> SEQUENCE: 3

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
            115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
            195                 200                 205

Gly Gly Gly Gly Glu Pro Lys Ser Ser Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
```

-continued

```
          355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
        435                 440
```

```
<210> SEQ ID NO 4
<211> LENGTH: 1411
<212> TYPE: DNA
<213> ORGANISM: Artificial Sequence
<220> FEATURE:
<223> OTHER INFORMATION: Cloning insert

<400> SEQUENCE: 4
aagcttgccg ccaccatgga atggtcctgg gtgttcctgt tcttcctgtc cgtgaccacc        60
ggcgtgcact ccaaagaggc ttgtcccacc ggcctgtaca cccactctgg cgagtgttgc       120
aaggcctgta acctgggaga aggcgtggcc cagccttgtg cgctaatca gacagtgtgc        180 gagccctgcc tggactccgt gaccttctcc gatgtggtgt ccgccaccga gccttgcaag       240
ccctgcacag agtgtgtggg cctgcagtcc atgtccgccc cttgcgtgga agccgacgac       300
gccgtgtgta gatcgcccta cggctactac caggacgaga caaccggcag atgcgaggcc       360
tgcagagtgt gcgaagctgg ctctggcctg gtgttcagtt gtcaagacaa gcagaacacc       420
gtgtgcgagg aatgccccga cggcacctac tctgacgagg ccaatcacgt ggacccctgc       480
ctgccttgca ccgtgtgtga agataccgag cggcagctgc gcgagtgcac cagatgggct       540
gatgccgagt gcgaagagat ccctggccgg tggatcacca gatccacccc tccagagggc       600
tccgactcta ccgctccctc tacccaggaa cctgaggccc tcctgagca ggacctgatc        660 gcttctacag tggccggcgt cgtgaccaca gtgatgggcg gaggcggcga gcctaagtcc       720
tccgacaaga cccacacctg tccccccttgt cctgcccctg aactgctggg cggaccttcc      780
gtgtttctgt tccccccaaa gcccaaggac accctgatga tctcccggac ccccgaagtg       840
acctgcgtgg tggtggatgt gtcccacgag gaccctgaag tgaagttcaa ttggtacgtg       900
gacggcgtgg aagtgcacaa cgccaagacc aagcccagag aggaacagta caactccacc       960
taccgggtgg tgtctgtgct gaccgtgctg caccaggact ggctgaacgg caaagagtac      1020
aagtgcaagg tgtccaacaa ggccctgcca gcccccatcg aaaagaccat ctccaaggcc      1080
aagggccagc cccgggaacc ccaggtgtac acactgcccc ctagcaggga cgagctgacc      1140
aagaaccagg tgtccctgac ctgtctcgtg aagggcttct accctccga tatcgccgtg       1200 gaatgggagt ccaacggcca gcctgagaac aactacaaga ccacccccc tgtgctggac       1260 agcgacggct cattcttct gtactccaag ctgacagtgg acaagtcccg gtggcagcag       1320
ggcaacgtgt tctcctgcag cgtgatgcac gaggctctgc acaaccacta cacccagaag      1380
tccctgtccc tgagccccgg ctgatgaatt c                                     1411
```

```
<210> SEQ ID NO 5
<211> LENGTH: 21
<212> TYPE: PRT
```

-continued

```
<213> ORGANISM: Artificial Sequence
<220> FEATURE:
<223> OTHER INFORMATION: Secretase site

<400> SEQUENCE: 5

Gly Ser Ser Gln Pro Val Val Thr Arg Gly Thr Thr Asp Asn Asp Ile
1               5                   10                  15

Glu Gly Arg Met Asp
            20

<210> SEQ ID NO 6
<211> LENGTH: 51
<212> TYPE: PRT
<213> ORGANISM: Artificial Sequence
<220> FEATURE:
<223> OTHER INFORMATION: Partial sequence for sequence alignment.

<400> SEQUENCE: 6

Ile Ala Ser Thr Val Ala Gly Val Val Thr Thr Val Met Gly Ser Ser
1               5                   10                  15

Gln Pro Val Val Thr Arg Gly Thr Thr Asp Asn Leu Ile Pro Val Tyr
            20                  25                  30

Cys Ser Ile Leu Ala Ala Val Val Val Gly Leu Val Ala Tyr Ile Ala
        35                  40                  45

Phe Lys Arg
    50

<210> SEQ ID NO 7
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 7

Ile Ala Ser Thr Val Ala Gly Val Val Thr Thr Val Met Gly Ile Pro
1               5                   10                  15

Lys Val Asp Lys Lys Val Glu Pro Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe
    50

<210> SEQ ID NO 8
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 8

Ile Ala Ser Thr Val Ala Gly Val Val Thr Thr Val Met Gly Ile Pro
1               5                   10                  15

Lys Val Asp Lys Lys Val Glu Pro Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe
    50
```

-continued

```
<210> SEQ ID NO 9
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 9

Ile Ala Ser Thr Val Ala Gly Val Val Thr Thr Val Met Gly Ile Pro
1               5                   10                  15

Lys Val Asp Lys Lys Val Glu Pro Lys Ser Ser Asp Lys Thr His Thr
                20                  25                  30

Cys Pro Pro Cys Pro Ala Pro Glu Leu Leu Gly Gly Pro Ser Val Phe
        35                  40                  45

Leu Phe
    50

<210> SEQ ID NO 10
<211> LENGTH: 45
<212> TYPE: PRT
<213> ORGANISM: Artificial Sequence
<220> FEATURE:
<223> OTHER INFORMATION: Partial sequence for sequence alignment

<400> SEQUENCE: 10

Ile Ala Ser Thr Val Ala Gly Val Val Thr Thr Val Met Gly Gly Gly
1               5                   10                  15

Gly Glu Pro Lys Ser Ser Asp Lys Thr His Thr Cys Pro Pro Cys Pro
                20                  25                  30

Ala Pro Glu Leu Leu Gly Gly Pro Ser Val Phe Leu Phe
        35                  40                  45

<210> SEQ ID NO 11
<211> LENGTH: 46
<212> TYPE: PRT
<213> ORGANISM: Artificial Sequence
<220> FEATURE:
<223> OTHER INFORMATION: Partial sequence for sequence alignment

<400> SEQUENCE: 11

Ile Ala Ser Thr Val Ala Gly Val Val Thr Thr Val Met Gly Gly Gly
1               5                   10                  15

Gly Ser Glu Pro Lys Ser Ser Asp Lys Thr His Thr Cys Pro Pro Cys
                20                  25                  30

Pro Ala Pro Glu Leu Leu Gly Gly Pro Ser Val Phe Leu Phe
        35                  40                  45

<210> SEQ ID NO 12
<211> LENGTH: 51
<212> TYPE: PRT
<213> ORGANISM: Artificial Sequence
<220> FEATURE:
<223> OTHER INFORMATION: Partial sequence for sequence alignment

<400> SEQUENCE: 12

Ile Ala Ser Thr Val Ala Gly Val Val Thr Thr Val Met Gly Gly Gly
1               5                   10                  15

Gly Ser Gly Gly Gly Gly Ser Glu Pro Lys Ser Ser Asp Lys Thr His
                20                  25                  30

Thr Cys Pro Pro Cys Pro Ala Pro Glu Leu Leu Gly Gly Pro Ser Val
        35                  40                  45

Phe Leu Phe
```

-continued

50

```
<210> SEQ ID NO 13
<211> LENGTH: 36
<212> TYPE: PRT
<213> ORGANISM: Artificial Sequence
<220> FEATURE:
<223> OTHER INFORMATION: Partial sequence for sequence alignment

<400> SEQUENCE: 13

Asn Thr Lys Val Asp Lys Lys Val Glu Pro Lys Ser Cys Asp Lys Thr
1               5                   10                  15

His Thr Cys Pro Pro Cys Pro Ala Pro Glu Leu Leu Gly Gly Pro Ser
                20                  25                  30

Val Phe Leu Phe
        35

<210> SEQ ID NO 14
<211> LENGTH: 427
<212> TYPE: PRT
<213> ORGANISM: Homo Sapiens

<400> SEQUENCE: 14

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Glu Gln Asp Leu Ile
        210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270
```

-continued

```
Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
        290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350

Gly Ser Ala Gly Asp Thr Trp Arg His Leu Ala Gly Glu Leu Gly Tyr
                355                 360                 365

Gln Pro Glu His Ile Asp Ser Phe Thr His Glu Ala Cys Pro Val Arg
        370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 15
<211> LENGTH: 250
<212> TYPE: PRT
<213> ORGANISM: Homo Sapiens

<400> SEQUENCE: 15

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
```

-continued

```
                210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn
                245                 250

<210> SEQ ID NO 16
<211> LENGTH: 221
<212> TYPE: PRT
<213> ORGANISM: Homo Sapiens

<400> SEQUENCE: 16

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
                20                  25                  30

Gln Thr Val Cys Glu Pro Cys Leu Asp Ser Val Thr Phe Ser Asp Val
            35                  40                  45

Val Ser Ala Thr Glu Pro Cys Lys Pro Cys Thr Glu Cys Val Gly Leu
        50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
                100                 105                 110

Lys Gln Asn Thr Val Cys Glu Glu Cys Pro Gly Thr Tyr Ser Asp Glu
                115                 120                 125

Ala Asn His Val Asp Pro Cys Leu Pro Cys Thr Val Cys Glu Asp Thr
        130                 135                 140

Glu Arg Gln Leu Arg Glu Cys Thr Arg Trp Ala Asp Ala Glu Cys Glu
145                 150                 155                 160

Glu Ile Pro Gly Arg Trp Ile Thr Arg Ser Thr Pro Pro Glu Gly Ser
                165                 170                 175

Asp Ser Thr Ala Pro Ser Thr Gln Glu Pro Glu Ala Pro Pro Glu Gln
                180                 185                 190

Asp Leu Ile Ala Ser Thr Val Ala Gly Val Val Thr Thr Val Met Gly
            195                 200                 205

Ser Ser Gln Pro Val Val Thr Arg Gly Thr Thr Asp Asn
        210                 215                 220

<210> SEQ ID NO 17
<211> LENGTH: 13
<212> TYPE: PRT
<213> ORGANISM: Homo Sapiens

<400> SEQUENCE: 17

Cys Ala Tyr Gly Tyr Tyr Gln Asp Glu Thr Thr Gly Arg
1               5                   10

<210> SEQ ID NO 18
<211> LENGTH: 49
<212> TYPE: PRT
<213> ORGANISM: Homo Sapiens

<400> SEQUENCE: 18

Val Cys Glu Ala Gly Ser Gly Leu Val Phe Ser Cys Gln Asp Lys Gln
1               5                   10                  15
```

-continued

```
Asn Thr Val Cys Glu Glu Cys Pro Gly Gly Thr Tyr Ser Asp Glu Ala
              20                  25                  30

Asn His Val Asp Pro Cys Leu Pro Cys Thr Val Cys Glu Asp Thr Glu
              35                  40                  45

Arg

<210> SEQ ID NO 19
<211> LENGTH: 15
<212> TYPE: PRT
<213> ORGANISM: Homo Sapiens

<400> SEQUENCE: 19

Val Cys Glu Ala Gly Ser Gly Leu Val Phe Ser Cys Gln Asp Lys
1               5                   10                  15

<210> SEQ ID NO 20
<211> LENGTH: 12
<212> TYPE: PRT
<213> ORGANISM: Homo Sapiens

<400> SEQUENCE: 20

Trp Ala Asp Ala Glu Cys Glu Glu Ile Pro Gly Arg
1               5                   10

<210> SEQ ID NO 21
<211> LENGTH: 17
<212> TYPE: PRT
<213> ORGANISM: Homo Sapiens

<400> SEQUENCE: 21

Leu Asp Ser Val Thr Ser Asp Val Val Ser Ala Thr Glu Pro Cys Lys
1               5                   10                  15

Pro

<210> SEQ ID NO 22
<211> LENGTH: 698
<212> TYPE: PRT
<213> ORGANISM: Homo Sapiens

<400> SEQUENCE: 22

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
              20                  25                  30

His Glu Ala Thr Lys Cys Gln Ser Phe Arg Asp His Met Lys Ser Val
              35                  40                  45

Ile Pro Ser Asp Gly Pro Ser Val Ala Cys Val Lys Lys Ala Ser Tyr
        50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                    85                  90                  95

Lys Pro Val Val Ala Glu Phe Tyr Gly Ser Lys Glu Asp Pro Gln Thr
              100                 105                 110

Phe Tyr Tyr Ala Val Ala Val Val Lys Lys Asp Ser Gly Phe Gln Met
              115                 120                 125

Asn Gln Leu Arg Gly Lys Lys Ser Cys His Thr Gly Leu Gly Arg Ser
        130                 135                 140
```

-continued

```
Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
                180                 185                 190

Cys Pro Gly Cys Gly Cys Ser Thr Leu Asn Gln Tyr Phe Gly Tyr Ser
                195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
                260                 265                 270

Arg Ser Met Gly Gly Lys Glu Asp Leu Ile Trp Glu Leu Leu Asn Gln
                275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
                340                 345                 350

Ala Pro Thr Asp Glu Cys Lys Pro Val Lys Trp Cys Ala Leu Ser His
                355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
    435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
                515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
```

-continued

```
              565              570              575
Asp Tyr Glu Leu Leu Cys Leu Asp Gly Thr Arg Lys Pro Val Glu Glu
            580              585              590

Tyr Ala Asn Cys His Leu Ala Arg Ala Pro Asn His Ala Val Val Thr
            595              600              605

Arg Lys Asp Lys Glu Ala Cys Val His Lys Ile Leu Arg Gln Gln Gln
            610              615              620

His Leu Phe Gly Ser Asn Val Thr Asp Cys Ser Gly Asn Phe Cys Leu
625              630              635              640

Phe Arg Ser Glu Thr Lys Asp Leu Leu Phe Arg Asp Asp Thr Val Cys
            645              650              655

Leu Ala Lys Leu His Asp Arg Asn Thr Tyr Glu Lys Tyr Leu Gly Glu
            660              665              670

Glu Tyr Val Lys Ala Val Gly Asn Leu Arg Lys Cys Ser Thr Ser Ser
            675              680              685

Leu Leu Glu Ala Cys Thr Phe Arg Arg Pro
690              695

<210> SEQ ID NO 23
<211> LENGTH: 609
<212> TYPE: PRT
<213> ORGANISM: Homo Sapiens

<400> SEQUENCE: 23

Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
            35              40              45

Ile Ala Phe Ala Gln Tyr Leu Gln Gln Cys Pro Phe Glu Asp His Val
            50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
            85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
            115             120             125

His Lys Asp Asp Asn Pro Asn Leu Pro Arg Leu Val Arg Pro Glu Val
            130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
            195             200             205

Leu Arg Asp Glu Gly Lys Ala Ser Ser Ala Lys Gln Arg Leu Lys Cys
            210             215             220

Ala Ser Leu Gln Lys Phe Gly Glu Arg Ala Phe Lys Ala Trp Ala Val
225             230             235             240
```

```
Ala Arg Leu Ser Gln Arg Phe Pro Lys Ala Glu Phe Ala Glu Val Ser
            245             250             255

Lys Leu Val Thr Asp Leu Thr Lys Val His Thr Glu Cys Cys His Gly
            260             265             270

Asp Leu Leu Glu Cys Ala Asp Asp Arg Ala Asp Leu Ala Lys Tyr Ile
            275             280             285

Cys Glu Asn Gln Asp Ser Ile Ser Ser Lys Leu Lys Glu Cys Cys Glu
        290             295             300

Lys Pro Leu Leu Glu Lys Ser His Cys Ile Ala Glu Val Glu Asn Asp
305             310             315             320

Glu Met Pro Ala Asp Leu Pro Ser Leu Ala Ala Asp Phe Val Glu Ser
            325             330             335

Lys Asp Val Cys Lys Asn Tyr Ala Glu Ala Lys Asp Val Phe Leu Gly
            340             345             350

Met Phe Leu Tyr Glu Tyr Ala Arg Arg His Pro Asp Tyr Ser Val Val
            355             360             365

Leu Leu Leu Arg Leu Ala Lys Thr Tyr Glu Thr Thr Leu Glu Lys Cys
            370             375             380

Cys Ala Ala Ala Asp Pro His Glu Cys Tyr Ala Lys Val Phe Asp Glu
385             390             395             400

Phe Lys Pro Leu Val Glu Glu Pro Gln Asn Leu Ile Lys Gln Asn Cys
            405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
            435             440             445

Glu Val Ser Arg Asn Leu Gly Lys Val Gly Ser Lys Cys Cys Lys His
        450             455             460

Pro Glu Ala Lys Arg Met Pro Cys Ala Glu Asp Tyr Leu Ser Val Val
465             470             475             480

Leu Asn Gln Leu Cys Val Leu His Glu Lys Thr Pro Val Ser Asp Arg
            485             490             495

Val Thr Lys Cys Cys Thr Glu Ser Leu Val Asn Arg Arg Pro Cys Phe
            500             505             510

Ser Ala Leu Glu Val Asp Glu Thr Tyr Val Pro Lys Glu Phe Asn Ala
            515             520             525

Glu Thr Phe Thr Phe His Ala Asp Ile Cys Thr Leu Ser Glu Lys Glu
            530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
        595             600             605

Leu
```

<210> SEQ ID NO 24
<211> LENGTH: 212
<212> TYPE: PRT
<213> ORGANISM: Homo Sapiens

<400> SEQUENCE: 24

-continued

```
Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asp Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210

<210> SEQ ID NO 25
<211> LENGTH: 326
<212> TYPE: PRT
<213> ORGANISM: Homo Sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
Met Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 26
<211> LENGTH: 165
<212> TYPE: PRT
<213> ORGANISM: Homo Sapiens

<400> SEQUENCE: 26

Cys Tyr Thr Leu Leu Leu Leu Thr Thr Pro Ser Trp Val Leu Ser Gln
1               5                   10                  15

Val Thr Leu Lys Glu Ser Gly Pro Val Leu Val Lys Pro Thr Glu Thr
            20                  25                  30

Leu Thr Leu Thr Cys Thr Val Ser Gly Phe Ser Leu Ser Asn Ala Lys
            35                  40                  45

Met Gly Val Ser Trp Ile Arg Gln Pro Pro Gly Lys Ala Leu Glu Trp
            50                  55                  60

Leu Ala His Ile Phe Ser Asn Asp Glu Lys Ser Tyr Ser Thr Ser Leu
65                  70                  75                  80

Lys Ser Arg Leu Thr Ile Ser Lys Asp Thr Ser Lys Ser Gln Val Val
                85                  90                  95

Leu Thr Met Thr Asn Met Asp Pro Val Asp Thr Ala Thr Tyr Tyr Cys
            100                 105                 110

Ala Arg Ile Phe Thr Ile Thr Tyr Ser Asn Tyr Val Leu Gln Tyr Tyr
            115                 120                 125

Tyr Tyr Met Asp Val Trp Gly Lys Gly Thr Thr Val Thr Val Ser Ser
            130                 135                 140

Ala Ser Thr Lys Gly Pro Ser Val Phe Pro Leu Ala Pro Cys Ser Arg
145                 150                 155                 160

Ser Thr Ser Gly Gly
                165
```

```
<210> SEQ ID NO 27
<211> LENGTH: 217
<212> TYPE: PRT
```

-continued

```
<213> ORGANISM: Homo Sapiens

<400> SEQUENCE: 27

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
    210                 215

<210> SEQ ID NO 28
<211> LENGTH: 209
<212> TYPE: PRT
<213> ORGANISM: Artificial
<220> FEATURE:
<223> OTHER INFORMATION: Engineered Fc Fragment

<400> SEQUENCE: 28

Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
            20                  25                  30

His Glu Asp Pro Glu Val Lys Phe Asn Trp Tyr Val Asp Gly Val Glu
            35                  40                  45

Val His Asn Ala Lys Thr Lys Pro Arg Glu Glu Gln Tyr Asn Ser Thr
        50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Asp Glu Leu Thr Lys Asn Gln Val
            115                 120                 125
```

-continued

```
Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser

<210> SEQ ID NO 29
<211> LENGTH: 225
<212> TYPE: PRT
<213> ORGANISM: Artificial
<220> FEATURE:
<223> OTHER INFORMATION: Engineered Fc Fragment

<400> SEQUENCE: 29

Thr His Thr Cys Pro Pro Cys Pro Ala Pro Glu Phe Glu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Ser Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
    210                 215                 220

Lys
225

<210> SEQ ID NO 30
<211> LENGTH: 5
<212> TYPE: PRT
<213> ORGANISM: Artificial
<220> FEATURE:
```

```
<223> OTHER INFORMATION: Linker peptide

<400> SEQUENCE: 30

Gly Gly Gly Gly Ser
1               5

<210> SEQ ID NO 31
<211> LENGTH: 5
<212> TYPE: PRT
<213> ORGANISM: Artificial
<220> FEATURE:
<223> OTHER INFORMATION: Linker peptide

<400> SEQUENCE: 31

Glu Ala Ala Ala Lys
1               5

<210> SEQ ID NO 32
<211> LENGTH: 5
<212> TYPE: PRT
<213> ORGANISM: Artificial
<220> FEATURE:
<223> OTHER INFORMATION: Linker peptide

<400> SEQUENCE: 32

Gly Gly Gly Gly Ser
1               5
```